(12) United States Patent
Yount et al.

(10) Patent No.: US 6,809,804 B1
(45) Date of Patent: Oct. 26, 2004

(54) SYSTEM AND METHOD FOR PROVIDING IMPROVED EVENT READING AND DATA PROCESSING CAPABILITIES IN A FLOW CYTOMETER

(75) Inventors: Dwayne Yount, Campbell, CA (US); Scott Brown, Santa Cruz, CA (US); Sreedhar Payavala, San Jose, CA (US); Willem Stokdijk, Livermore, CA (US); Perry Hopkins, Fremont, CA (US); Steven Helms, Scottsdale, AZ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 34 days.

(21) Appl. No.: 09/853,043

(22) Filed: May 11, 2001

Related U.S. Application Data

(60) Provisional application No. 60/203,515, filed on May 11, 2000, provisional application No. 60/203,590, filed on May 11, 2000, provisional application No. 60/203,585, filed on May 11, 2000, and provisional application No. 60/203,577, filed on May 11, 2000.

(51) Int. Cl.[7] .......................... G01N 15/14; G01N 21/00
(52) U.S. Cl. ................... 356/73; 250/574; 250/214 DC
(58) Field of Search .......................... 356/73, 336, 338, 356/340, 432, 435, 442; 250/574, 576, 461.2, 214 DC; 209/576, 577, 579, 588; 422/68.1, 82.05; 702/21, 79

(56) References Cited

U.S. PATENT DOCUMENTS

| 3,344,406 A | 9/1967 | Vinal |
| 3,373,437 A | 3/1968 | Sweet et al. |
| 3,454,953 A | 7/1969 | Lloyd et al. |
| 3,596,275 A | 7/1971 | Sweet |
| 3,609,379 A | 9/1971 | Hildebrandt |
| 3,719,086 A | 3/1973 | Bannister et al. |
| 3,872,730 A | 3/1975 | Ringrose et al. |
| 3,885,438 A | 5/1975 | Harris, Sr. et al. |
| 3,954,341 A | 5/1976 | Uffenheimer |
| 3,960,449 A | 6/1976 | Carleton et al. |
| 4,000,973 A | 1/1977 | Petersen |
| 4,244,919 A | 1/1981 | Chen |
| 4,269,703 A | 5/1981 | Brüderlein |
| 4,311,484 A | 1/1982 | Fosslien |
| 4,313,735 A | 2/1982 | Yamashita et al. |
| 4,347,935 A | 9/1982 | Merrill |
| 4,357,301 A | 11/1982 | Cassaday et al. |
| 4,367,043 A | 1/1983 | Sweet et al. |

(List continued on next page.)

FOREIGN PATENT DOCUMENTS

| EP | 0645631 | 3/1995 |
| WO | 0126718 | 11/1984 |
| WO | 8404672 | 12/1984 |

OTHER PUBLICATIONS

Van den Engh and Stokdijk, Parallel Processing Data Acquisition System for Multilaser Flow Cytometry and Cell Sorting, Cytometry, vol. 10:282–293 (1989).

Data Conversion Seminar, Analog Devices, Inc., pp. 11–36 through 11–38 (1982).

Linear Databook, National Semiconductor Corporation, pp. 8–10 through 8–20 (1978).

*Primary Examiner*—Thanh X. Luu
*Assistant Examiner*—Seung C. Sohn
(74) *Attorney, Agent, or Firm*—Douglas A. Petty

(57) ABSTRACT

A system and method for use with a flow cytometer to improve event reading and data processing capabilities of the flow cytometer, while also providing efficient system configuration assessment capabilities. The system and method enables the flow cytometer to capture and sample an entire waveform representative of an event being read, and provides improved processing and analysis of the sampled data in a real time or near real-time basis. The system and method further enable the flow cytometer to assess its configuration and provide assessment results to an operator in an efficient and effective manner.

31 Claims, 25 Drawing Sheets

U.S. PATENT DOCUMENTS

| | | | |
|---|---|---|---|
| 4,475,411 A | 10/1984 | Wellerfors | |
| 4,517,850 A | 5/1985 | Wiseman et al. | |
| 4,525,673 A | 6/1985 | Berkowitz | |
| 4,599,307 A | 7/1986 | Saunders et al. | |
| 4,602,995 A | 7/1986 | Cassaday et al. | |
| 4,660,971 A | 4/1987 | Sage et al. | |
| 4,667,830 A | 5/1987 | Nozaki, Jr. et al. | |
| 4,669,060 A | 5/1987 | Therond et al. | |
| 4,673,404 A | 6/1987 | Gustavsson | |
| 4,683,212 A | 7/1987 | Uffenheimer | |
| 4,704,891 A | 11/1987 | Recktenwald et al. | |
| 4,727,020 A | 2/1988 | Recktenwald | |
| 4,748,573 A | 5/1988 | Sarandrea et al. | |
| 4,756,201 A | 7/1988 | Uffenheimer | |
| 4,758,409 A | 7/1988 | Uffenheimer | |
| 4,764,687 A | 8/1988 | Hamilton et al. | |
| 4,774,057 A | 9/1988 | Uffenheimer et al. | |
| 4,799,393 A | 1/1989 | Uffenheimer | |
| 4,808,381 A | 2/1989 | McGregor et al. | |
| 4,811,611 A | 3/1989 | Uffenheimer | |
| 4,813,031 A * | 3/1989 | Bierhoff | 369/44.34 |
| 4,836,038 A | 6/1989 | Baldwyn | |
| 4,863,066 A | 9/1989 | Uffenheimer et al. | |
| 4,867,908 A | 9/1989 | Recktenwald et al. | |
| 4,907,229 A | 3/1990 | Edwards et al. | |
| 4,928,539 A | 5/1990 | Champseix et al. | |
| 4,943,926 A | 7/1990 | Guzman-Edery et al. | |
| 4,984,475 A | 1/1991 | Uffenheimer et al. | |
| 4,987,086 A | 1/1991 | Brosnan et al. | |
| 4,987,539 A | 1/1991 | Moore et al. | |
| 4,989,977 A | 2/1991 | North, Jr. | |
| 4,997,768 A | 3/1991 | Uffenheimer et al. | |
| 5,010,560 A | 4/1991 | Janney et al. | |
| 5,012,845 A | 5/1991 | Averette | |
| 5,101,673 A | 4/1992 | Uffenheimer et al. | |
| 5,133,218 A | 7/1992 | Uffenhiemer et al. | |
| 5,150,313 A * | 9/1992 | van den Engh et al. | 702/79 |
| 5,201,232 A | 4/1993 | Uffenheimer | |
| 5,215,714 A | 6/1993 | Okada et al. | |
| 5,229,074 A | 7/1993 | Heath et al. | |
| 5,231,426 A | 7/1993 | Sweet | |
| 5,464,581 A | 11/1995 | Van den Engh | |
| 5,466,572 A | 11/1995 | Sasaki et al. | |
| 5,483,469 A | 1/1996 | Van den Engh et al. | |
| 5,485,639 A | 1/1996 | Cavazos | |
| 5,602,039 A | 2/1997 | Van den Engh | |
| 5,602,349 A | 2/1997 | Van den Engh | |
| 5,643,796 A | 7/1997 | Van den Engh et al. | |
| 5,675,517 A | 10/1997 | Stokdijk | |
| 5,682,038 A | 10/1997 | Hoffman | |
| 5,700,692 A | 12/1997 | Sweet | |
| 5,726,364 A | 3/1998 | Van den Engh | |
| 5,726,404 A | 3/1998 | Brody | |
| 5,726,751 A | 3/1998 | Altendorf et al. | |
| 5,845,639 A | 12/1998 | Hochman et al. | |
| 5,880,474 A | 3/1999 | Norton et al. | |
| 6,014,904 A | 1/2000 | Lock | |
| 6,046,807 A | 4/2000 | Chandler | |
| 6,139,800 A | 10/2000 | Chandler | |
| 6,221,671 B1 * | 4/2001 | Groner et al. | 436/63 |
| 6,366,354 B1 | 4/2002 | Chandler | |
| 6,411,904 B1 | 6/2002 | Chandler | |

* cited by examiner

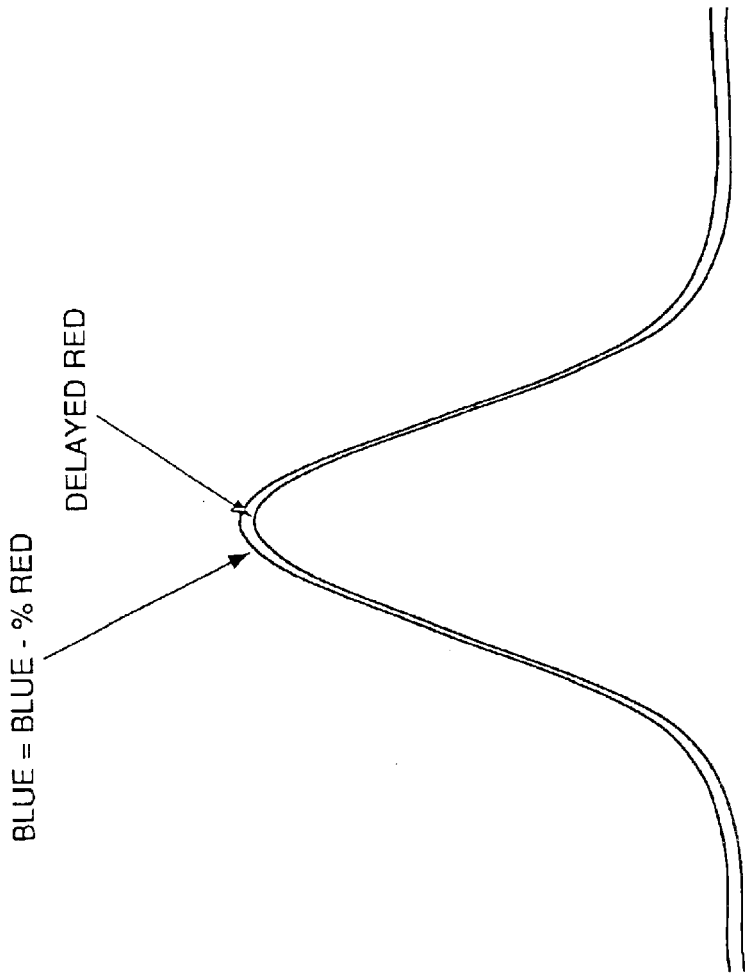

SYSTEM AND METHOD FOR PROVIDING IMPROVED EVENT READING AND DATA PROCESSING CAPABILITIES IN A FLOW CYTOMETER

The present invention claims benefit under 35 U.S.C §119(e) of a U.S. Provisional Patent Application of Dwayne Yount et al. entitled "Hardware and Electronics Architecture for a Flow Cytometer", Ser. No. 60/203,515, filed May 11, 2000, of a U.S. Provisional Patent Application of Michael Lock et al. entitled "Cluster Finder Algorithm for Flow Cytometer", Ser. No. 60/203,590, filed May 11, 2000, of a U.S. Provisional Patent Application of Michael Goldberg et al. entitled "User Interface and Network Architecture for Flow Cytometer", Ser. No. 60/203,585, filed May 11, 2000, and of a U.S. Provisional Patent Application of John Cardott et al. entitled "Digital Flow Cytometer", Ser. No. 60/203, 577, filed May 11, 2000, the entire contents of each of said provisional patent applications being incorporated herein by reference.

CROSS-REFERENCE TO RELATED APPLICATIONS

Related subject matter is disclosed in a copending U.S. Patent Application of Pierce O. Norton entitled "Apparatus and Method for Verifying Drop Delay in a Flow Cytometer", Ser. No. 09/346,692, filed Jul. 2, 1999, in a copending U.S. Patent Application of Kenneth F. Uffenheimer et al. entitled "Apparatus and Method for Processing Sample Materials Contained in a Plurality of Sample Tubes", Ser. No. 09/447, 804, filed Nov. 23, 1999, and in a copending U.S. Patent Application of Michael D. Lock et al. entitled "System for Identifying Clusters in Scatter Plots Using Smoothed Polygons with Optimal Boundaries", Ser. No. 09/853,037, filed even date herewith, the entire contents of each of these applications are incorporated herein by reference.

BACKGROUND OF THE INVENTION

1. Field of the Invention

The present invention relates to a system and method for providing improved event reading, data processing and system configuration capabilities in a flow cytometer. In particular, the present invention provides a system and method for use with a flow cytometer that enables the event reading components of the flow cytometer to capture and digitize substantially the entire optical waveform of each detected event, and provides improved, near real-time processing of the digitized waveform data and automated system configuration assessment capabilities.

2. Description of the Related Art

Flow cytometers known in the art are used for analyzing and sorting particles in a fluid sample, such as cells of a blood sample or particles of interest in any other type of biological or chemical sample. A flow cytometer typically includes a sample reservoir for receiving a fluid sample, such as a blood sample, and a sheath reservoir containing a sheath fluid. The flow cytometer transports the particles (hereinafter called "cells") in the fluid sample as a cell stream to a flow cell, while also directing the sheath fluid to the flow cell.

Within the flow cell, a liquid sheath is formed around the cell stream to impart a substantially uniform velocity on the cell stream. The flow cell hydrodynamically focuses the cells within the stream to pass through the center of a laser beam. The point at which the cells intersect the laser beam, commonly known as the interrogation point, can be inside or outside the flow cell. As a cell moves through the interrogation point, it causes the laser light to scatter. The laser light also excites components in the cell stream that have fluorescent properties, such as fluorescent markers that have been added to the fluid sample and adhered to certain cells of interest, or fluorescent beads mixed into the stream.

The flow cytometer further includes an appropriate detection system consisting of photomultipliers tubes, photodiodes or other light detecting devices, which are focused at the intersection point. The flow cytometer analyzes the detected light to measure physical and fluorescent properties of the cell. The flow cytometer can further sort the cells based on these measured properties.

To sort cells by an electrostatic method, the desired cell must be contained within an electrically charged droplet. To produce droplets, the flow cell is rapidly vibrated by an acoustic device, such as a piezoelectric element. The droplets form after the cell stream exits the flow cell and at a distance downstream from the interrogation point. Hence, a time delay exists from when the cell is at the interrogation point until the cell reaches the actual break-off point of the droplet. The magnitude of the time delay is a function of the manner in which the flow cell is vibrated to produce the droplets, and generally can be manually adjusted, if necessary.

To charge the droplet, the flow cell includes a charging element whose electrical potential can be rapidly changed. Due to the time delay which occurs while the cell travels from the interrogation point to the droplet break-off point, the flow cytometer must invoke a delay period between when the cell is detected to when the electrical potential is applied to the charging element. This charging delay is commonly referred to as the "drop delay", and should coincide with the travel time delay for the cell between the interrogation point and the droplet break-off point to insure that the cell of interest is in the droplet being charged.

At the instant the desired cell is in the droplet just breaking away from the cell stream, the charging element is brought up to the appropriate potential, thereby causing the droplet to isolate the charge once it is broken off from the stream. The electrostatic potential from the charging circuit cycles between different potentials to appropriately charge each droplet as it is broken off from the cell stream.

Because the cell stream exits the flow cell in a substantially downward vertical direction, the droplets also propagate in that direction after they are formed. To sort the charged droplet containing the desired cell, the flow cytometer includes two or more deflection plates held at a constant electrical potential difference. The deflection plates form an electrostatic field which deflects the trajectory of charged droplets from that of uncharged droplets as they pass through the electrostatic field. Positively charged droplets are attracted by the negative plate and repelled by the positive plate, while negatively charged droplets are attracted to the positive plate and repelled by the negative plate. The lengths of the deflection plates are small enough so that the droplets which are traveling at high velocity clear the electrostatic field before striking the plates. Accordingly, the droplets and the cells contained therein can be collected in appropriate collection vessels downstream of the plates.

Known flow cytometers similar to the type described above are described, for example, in U.S. Pat. Nos. 3,960, 449, 4,347,935, 4,667,830, 5,464,581, 5,483,469, 5,602,039, 5,643,796 and 5,700,692, the entire contents of each patent being incorporated by reference herein. Other types of known flow cytometer, are the FACSVantage™, FACSort™, FACSCount™, FACScan™ and FACSCalibur ™ systems, each manufactured by Becton Dickinson and Company, the assignee of the present invention.

Although the flow cytometers described above can be suitable for reading events as intended, these existing systems do suffer from certain drawbacks. For example, in these types of instruments, the controller or central processing unit (CPU) does not ordinarily process the data obtained from reading the events in "real time". However, it is desirable to process the data in real time or near real time to improve the efficiency of the flow cytometer and the ability to compare the readings of the events on a real-time or near real-time basis.

These existing systems also do not capture the entire image of the event. That is, when each event is read by detecting, for example, light fluorescing from the cell or particle of interest, these systems capture the "peak point" or peak intensity of the detected light. These systems also typically measure the duration during which the light is detected. By detecting these two parameters, the existing systems can use this data to determine characteristics of the event, such as the identity and size of a cell of interest. However, these techniques do not enable the existing systems to sample individual regions of the cell or particle of interest, nor are they capable of being performed on a real-time or near real-time basis. Furthermore, these systems are typically incapable of comparing data from multiple events effectively and in a real time or near real-time manner.

In addition, these types of existing systems do not provide a mechanism that indicates the configuration of the system to the operator effectively. For example, these types of systems are typically configured with multiple detector and filter arrangements that enable the different detectors to detect light having wavelengths within different wavelength regions. In such an arrangement, one detector can detect light with having a wavelength within the range of blue light, for example, while another detector can detect light having a wavelength within the range of green light. However, if an incorrect filter is placed in front of a particular detector, the detector will detect the incorrect light (e.g., green light instead of blue light). The system will therefore give erroneous results. However, the operator of the system will have difficulty determining which filters are arranged incorrectly, and in the worst case, the error may go unnoticed.

Accordingly, a need exists for an improved system and method for use with a flow cytometer to improve the event reading and data processing features of the flow cytometer to eliminate the above drawbacks.

SUMMARY OF THE INVENTION

An object of the present invention is to provide a system and method for use with a flow cytometer to improve event reading and data processing capabilities of the flow cytometer, while also providing efficient system configuration assessment capabilities.

Another object of the present invention is to provide a system and method that enables a flow cytometer to capture and sample an entire waveform representative of an event being read, and which provides improved processing and analysis of the sampled data in a real-time or near real-time basis.

A further object of the present invention is to provide a system and method that is capable of indicating the configuration of a flow cytometer to an operator in an efficient and effective manner.

These and other objects are substantially achieved by providing a system and method for processing at least one signal representative of an event detected by at least one detector in a flow cytometer. The system and method employs a sampling device which is adapted to receive portions of the signal from the detector in time sequence and to generate a respective value representative of the respective magnitude of each respective portion of the signal as the respective portion of the signal is being received. The system and method further employ a storage device which is adapted to store the values generated by the sampling device. The sampling device can receive substantially all of the signal, and can generate the values which represent the portions of substantially all of the signal. The signal can be an analog signal representative of a light signal emitted from the event as detected by the detector. The system and method can further employ an arithmetic device which is adapted to, for example, subtract a designated value from each of the values generated by the sampling device. The designated value can be representative of an unwanted signal, such as crosstalk, detected by the detector, or can be representative of a characteristic of the detector. The sampling device can further be adapted to receive portions of a second signal from a second detector in time sequence and to generate a respective second value representative of the respective magnitude of each respective portion of the second signal as the respective portion of the second signal is being received, and the storage device can store the second values generated by the sampling device. The sampling device can receive the portions of the signal at a time different from that during which it receives at least some of the portions of the second signal, and the system and method can employ a comparator which is adapted to compare each of the second values with a respective one of the values to compare the signal to the second signal.

These and other objects are further substantially achieved by providing a system and for identifying a configuration of a detector unit of a flow cytometer. The system and method employ a port which is adapted to couple to a removable device that includes an optical clement, such as a mirror or filter, and a memory adapted to store information pertaining to the optical element. The system and method further employ a reader which is adapted to read the information stored in the memory when the removable device is coupled to the port. The system and method can also employ an indicator which adapted to provide an indication of the information read by the reader.

These and other objects are also substantially achieved by providing a removable device which is adapted for coupling with a port of a flow cytometer, and comprises an optical element, such as a filter or mirror, and a memory adapted to store information pertaining to the optical element.

BRIEF DESCRIPTION OF THE DRAWINGS

The various objects, advantages and novel features of the present invention will now be more readily appreciated from the following detailed description when read in conjunction with the accompanying drawings, in which:

FIGS. 23–27 illustrate exemplary waveforms and their processing by the circuitry shown in FIGS. 11 and 12.

DETAILED DESCRIPTION OF THE PREFERRED EMBODIMENTS

Figure 1:
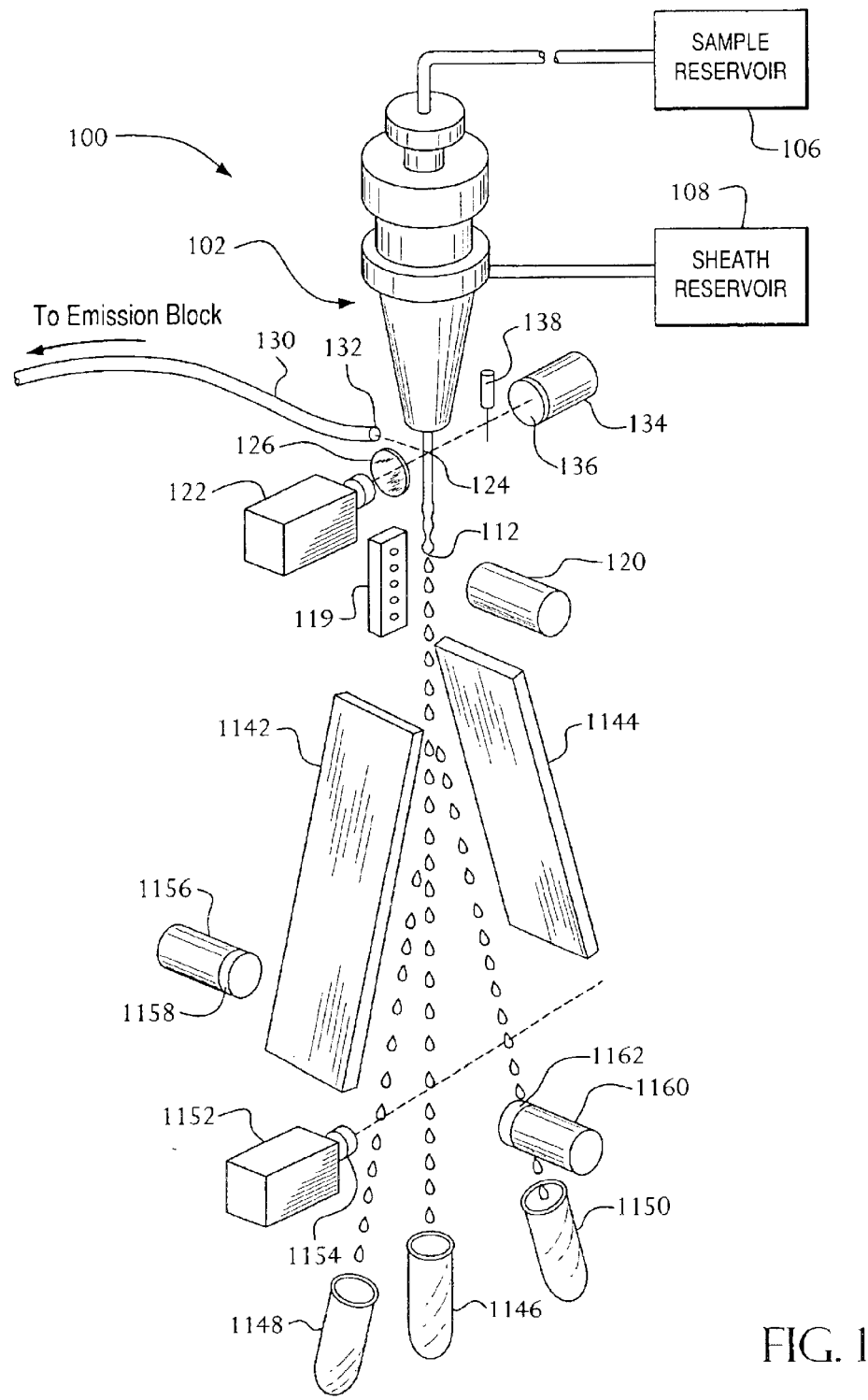
FIG. 1 is a conceptual block diagram of the flow cytometer employing a system and method according to an embodiment of the present invention.
Figure 2:
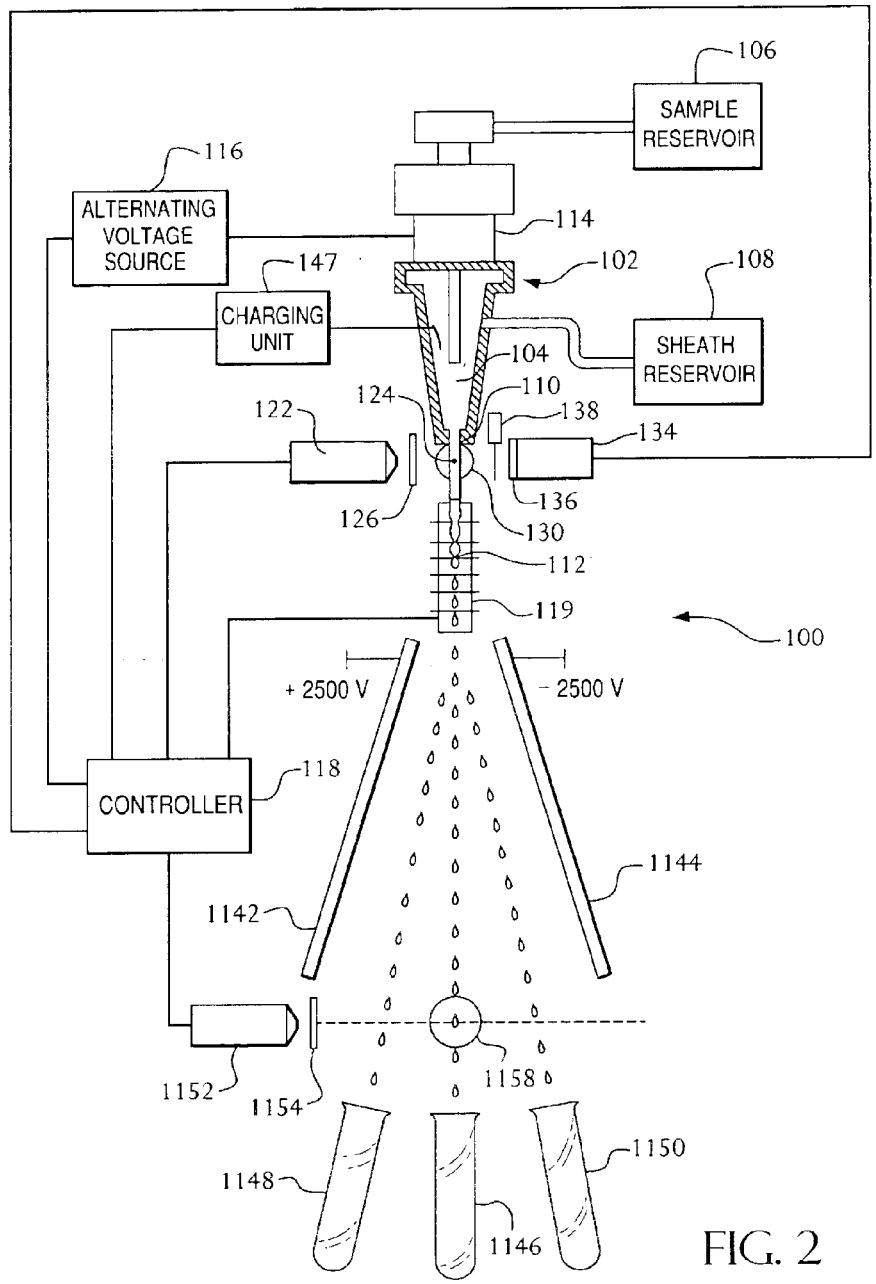
FIG. 2 is a cross-sectional view of the flow cytometer shown in FIG. 1.

A flow cytometer 100 employing an embodiment of the present invention is illustrated in FIGS. 1 and 2. As discussed in the background section above, the flow cytometer 100 includes a nozzle 102 having a flow cell 104 therein. The flow cytometer further includes a sample reservoir 106 for receiving a fluid sample, such as a blood sample, and a sheath reservoir 108 containing a sheath fluid. The flow cytometer transports the cells in the fluid sample in the cell stream to the flow cell 104, while also directing the sheath fluid to the flow cell 104.

Within the flow cell 104, the sheath fluid surrounds the cell stream, and the combined sheath fluid and cell stream exits the flow cell 104 via an opening 110 as a sample stream. The opening 110 can have a diameter of, for example, 50 μm, 70 μm, 100 μm, or any other suitable diameter. As illustrated, due to characteristics of the sheath fluid, such as surface tension and the like, the sample stream remains intact until breaking off into droplets at the droplet break-off point 112, which is at a certain distance from opening 110. The distance from opening 110 at which the droplet break-off point 112 occurs, and the frequency or rate at which the droplets are formed, are governed by the fluid pressure, as well as the amplitude and frequency of oscillation of oscillating device 114 which can be, for example, a piezoelectric element.

As shown in FIG. 2, the oscillating device 114 is connected to an alternating voltage source 116 whose output voltage amplitude, frequency and phase is controlled by a controller 118 which can include, for example, a microprocessor or any other suitable controlling device. Further details of the controller 118 are described below. The amplitude of the alternating voltage signal output by alternating voltage source 116 can be increased or decreased by controller 118 to in turn increase or decrease the distance from opening 110 at which the droplet break-off 112 occurs. Likewise, the frequency of the alternating voltage signal output by alternating voltage source 116 can be increased or decreased by controller 118 to increase or decrease the rate at which droplets of sample fluid are formed at the droplet break-off point 112.

To view the droplet break-off point 112, a light source 119, such an LED array, can be positioned in the region of the sample fluid stream containing the droplet break-off point 112. The controller 118 can control the light source 119 to strobe at a described frequency, so that the detector 120, such as a camera or other special viewing device, can be used to view the region of the sample fluid stream containing the droplet break-off point 112. The flow cytometer 100 further includes at least one laser 122, such as a diode laser, which is controlled by controller 118 to emit laser light. The emitted laser light intersects the sample stream at a point of interest 124 commonly referred to as a the interrogation point.

The laser 122 can be, for example, a red laser that emits light having a wavelength of at or about 633 nm, which is in the red light spectrum. Alternatively, laser 122 can be a blue laser that emits light having a wavelength of at or about 488 nm, which is in the blue light spectrum. Laser 122 also can be an ultraviolet laser that emits light having a wavelength of at or about 325 nm, or within the range of at or about 351 nm to at or about 364 nm, all of which are within the ultraviolet spectrum. As discussed in more detail below, flow cytometer 100 can include multiple lasers 122 that each emit their respective laser light to a respective interrogation point along the fluid flow stream. Also, if desired, a lens or filter 126 can be positioned between the laser 122 and the interrogation point 124 to filter out light of unwanted wavelengths from the laser light prior to its reaching the interrogation point 124.

As further illustrated, the flow cytometer includes at least one fiberoptic cable 130 that receives laser light that has intersected the sample stream at the interrogation point 124 and has been scattered by the sample stream fluid and, in particular, by any cells or particles of interest present in the sample stream. The input port 132 of the fiberoptic cable 130 in this example is located in the same plane as the laser light being emitted from laser 122, and at a 90° angle or about a 90° angle with respect to the direction of propagation of the laser light being emitted from laser 122. The laser light scattered by the fluid stream and any cells or particles of interest at the interrogation point 124 is commonly referred to as side-scatter laser light.

As further illustrated, a detector 134 and filter 136 arrangement can be used to detect a portion of the laser light that has passed through the interrogation point 124 along the direction of propagation of the laser light being emitted by laser 122, which is commonly referred to as the forward-scatter laser light. Also, if desired, an obscuration bar 138 can be position in the path of the forward-scatter laser light, in the path of the side-scatter laser light, or in both paths, to reduce the amount of side-scatter laser light entering fiber optic cable 130 or to reduce the amount of forward-scatter laser light entering detector 134. The side-scatter laser light entering the fiberoptic cable 130 is input to an emission block 140 as described in more detail below.

As further shown in FIGS. 1 and 2, the flow cytometer 100 can include deflection plates 1142 and 1144 which can be controlled by controller 118 to allow droplets to pass to droplet collection container 1146, or to deflect droplets that have been charged by charging unit 147 towards droplet collection containers 1148 and 1150, as appropriate. In additional, a laser and filter arrangement 1152 and 1154, detector and filter arrangement 1156 and 1158, and detector and filter arrangement 1160 and 1162, can be employed to monitor the manner in which the droplets are being deflected. Further details of the charging, deflection, and monitoring of the droplets are described in copending U.S. patent application Ser. No. 09/346,692, referenced above.

Further details of the emission block 140 will now be discussed with reference to FIGS. 3–10. As illustrated, emission block 140 includes a support ring 142 which can be made from stainless steel or any other suitable material. As shown, in particular, in FIGS. 4–6, support ring 142 has inner groves 144 in its inner surface and outer groves 146 in its outer surface. A first flex circuit 148 is mountable in support ring 142. Specifically, the first flex circuit 148 includes projections 150 that are received into inner groves 144 of support ring 142 to thus mount the first flex circuit 148 inside support ring 142. As can be appreciated by one skilled in the art, first flex circuit 148 is an integrated circuit board arrangement that includes a plurality of integrated circuits (not shown) and contact pads 152 that have contacts 154 which are adapted to provide connections to the circuitry in the first flex circuit 148.

As further illustrated, a second flex circuit 156 is mountable to the support ring 142. That is, the second flex circuit 156 includes projections 158 that can be received in the outer groves 146 of the support ring 142 to thus mount the second flex circuit 156 to the exterior of support ring 142. An adhesive can be used to secure the first flex circuit 148 and the second flex circuit 156 to the support ring 142. Like first flex circuit 148, second flex circuit 156 is also an integrated circuit arrangement that includes integrated circuits 160 that are capable of carrying out certain data processing operation as discussed in more detail below. The second flex circuit 156 further includes contact pads 162 that include contacts 164 which provide connections to the circuitry in the second flex circuit 156.

Figure 7:
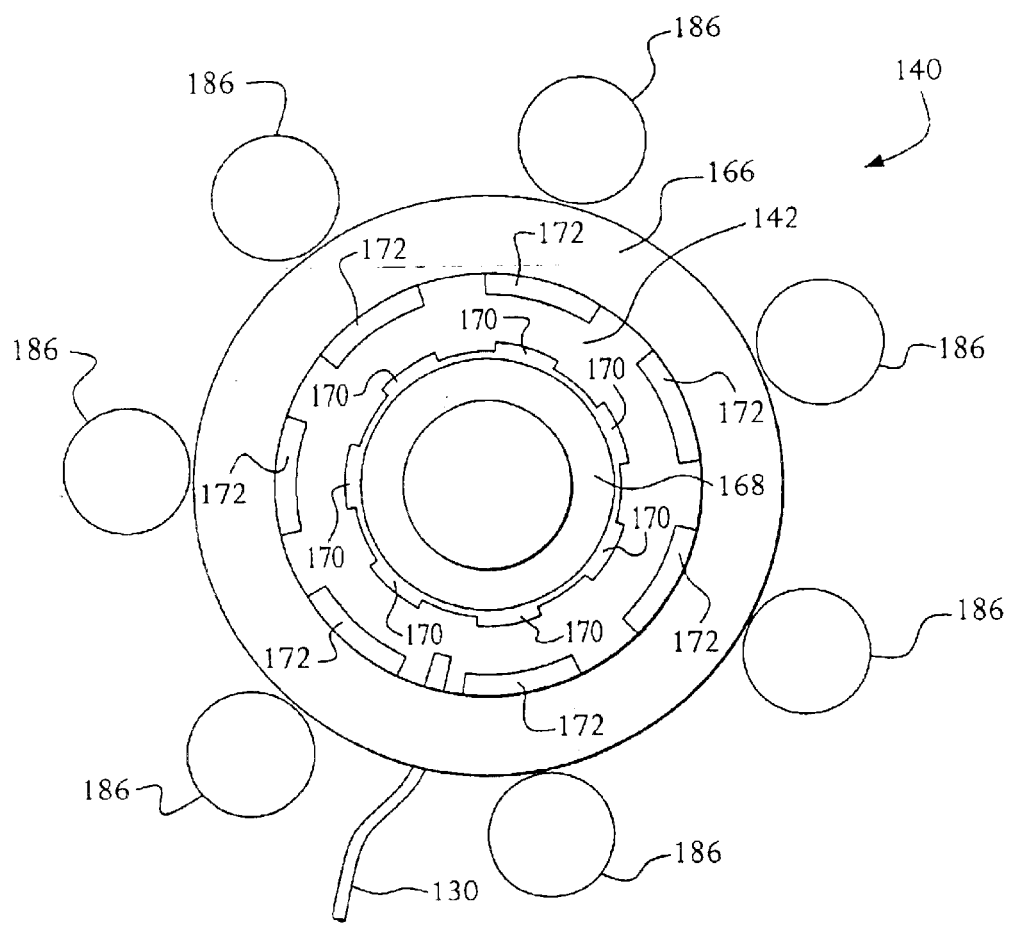
FIG. 7 is a conceptual top plan view of the emission block shown in FIG. 3.

As further illustrated, the emission block 140, first flex circuit 148 and second flex circuit 156 are housed within an outer housing 166 and inner housing 168. As illustrated, the combination of the support ring 142, first flex circuit 148, second 156, outer housing 166 and inner housing 168 form openings 170 and 172 as illustrated in FIG. 7. Each of the openings 170 is configured to receive a mirror assembly 174 which includes a dichroic mirror 176, the purpose of which is described in more detail below. Furthermore, each opening 172 is configured to receive a filter assembly 180, the purpose of which is described in more detail below. In this example, emission block 140 is capable of receiving six mirror assemblies 174-1 through 174-6 and seven filter assemblies 180-1 through 180-7 (see FIGS. 7 and 10). However, the emission block 140 can be configured to include any suitable number of mirror assemblies 174 and filter assemblies 180.

Figure 8:
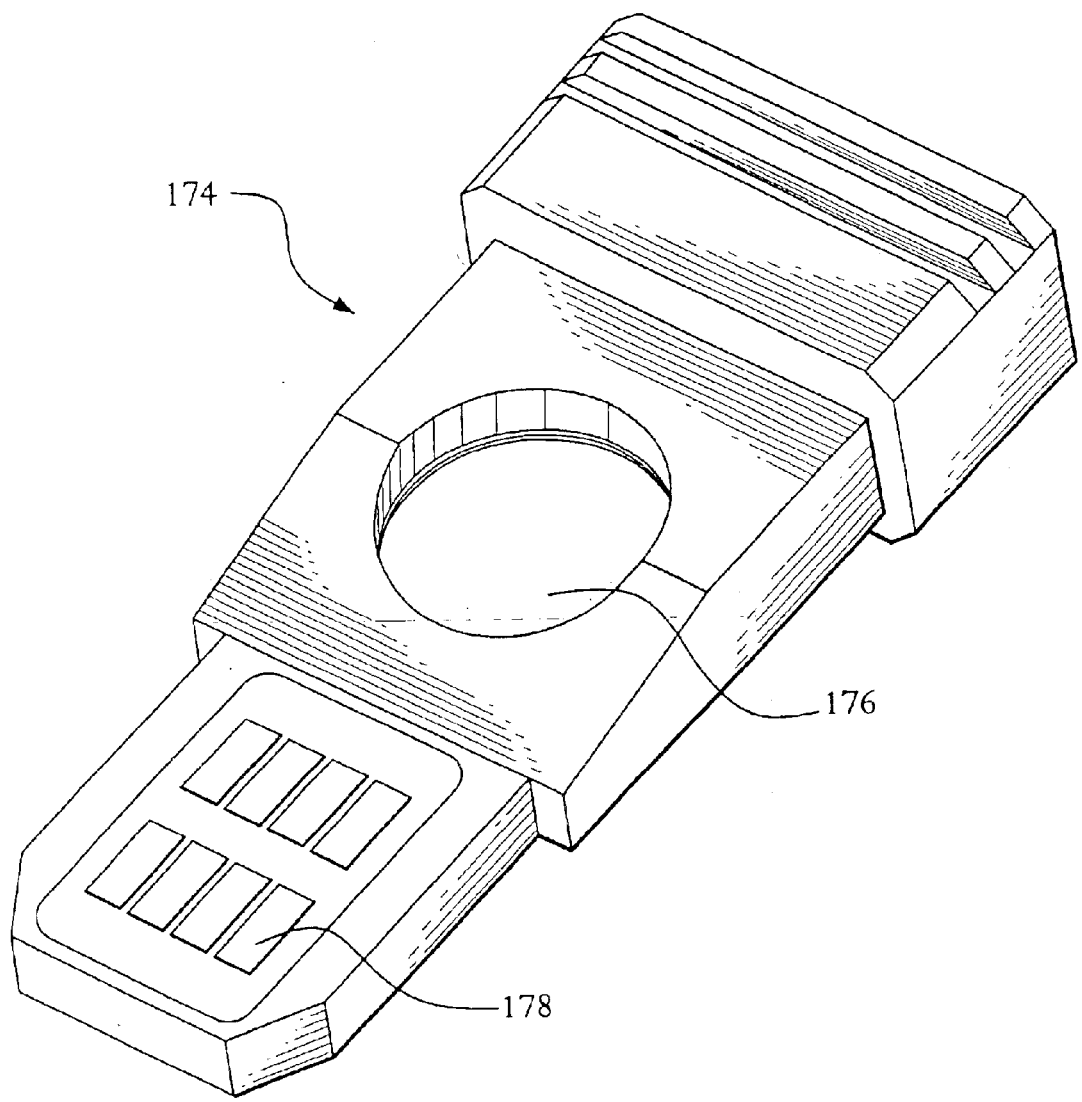
FIG. 8 is a perspective view of an example of a removable mirror assembly for use with the emission block shown in FIG. 3 in accordance with an embodiment of the present invention.

An example of a mirror assembly 174 is shown in FIG. 8. As stated above, each mirror assembly 174 includes a dichroic mirror 176 that is capable of passing light having a particular wavelength (e.g., blue light) while reflecting light of all other wavelengths. The diachronic mirror assembly 174 includes a memory, such as an electrically, erasable read-only memory (EEPROM), in which is stored information pertaining to the type of dichroic mirror 176 in the mirror assembly 174, along with other information such as the company of manufacture, the date and place of manufacture and so on, for purposes described in more detail below. The mirror assembly 174 further includes contacts 178 that provide electrical connection with the memory embedded in the mirror assembly 174. Accordingly, when the mirror assembly 174 is inserted into an opening 170 as shown, for example, in FIG. 7, the contacts 178 of mirror assembly 174 engage with the contact 154 on the contact pads 152 of the first flex circuit 148. Accordingly, the circuitry in the first flex circuit 148 can thus access the information stored in the memory of the mirror assembly 174 for the purposes described in more detail below.

Figure 9:
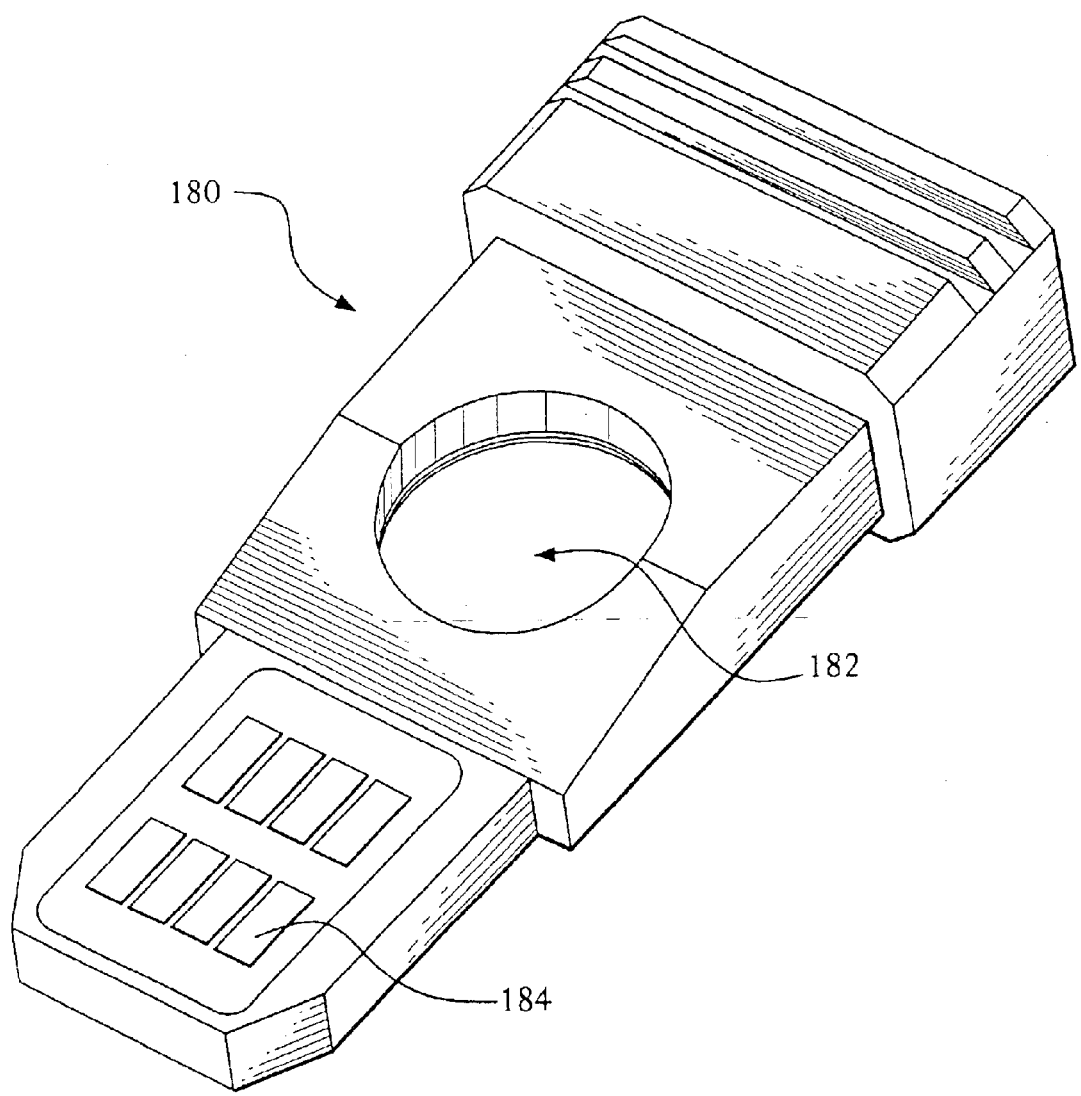
FIG. 9 is a perspective view of an example of a removable mirror assembly for use with the emission block shown in FIG. 3 in accordance with an embodiment of the present invention.

A filter assembly 180 is shown in more detail in FIG. 9. Filter assembly 180 includes a filter 182 that is capable of passing light of a certain wavelength (e.g., blue light) while blocking light of all other wave lengths. Furthermore, like mirror assembly 174, filter assembly 180 includes a memory, such as ROM, in which is stored information pertaining to the type of filter 182 in the filter assembly 180, the date, place, and company of manufacture, and so on. Filter assembly 180 also includes contacts 184 which provide electrical contact to the memory embedded in the filter assembly 180. Accordingly, when the filter assembly 180 is inserted into an opening 172 as shown, for example, in FIG. 7, the contacts 184 of the filter assembly 180 engage with the contacts 164 on a contact pad 162 of the second flex circuit 156. Hence, the circuitry in the second flex circuit 156 can then access the information stored in the memory of the filter assembly 180 for reasons discussed below.

Figure 3:
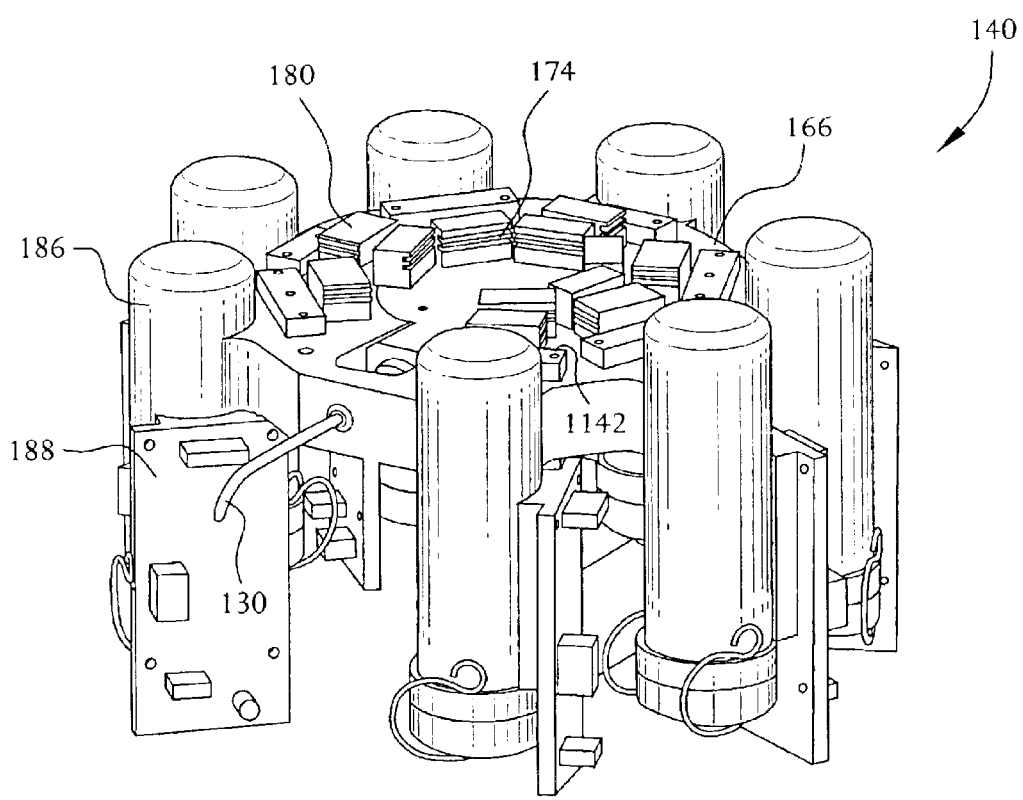
FIG. 3 is a detailed view of an example of an emission block according to an embodiment of the present invention which is employed in the flow cytometer shown in FIGS. 1 and 2.
Figure 4:
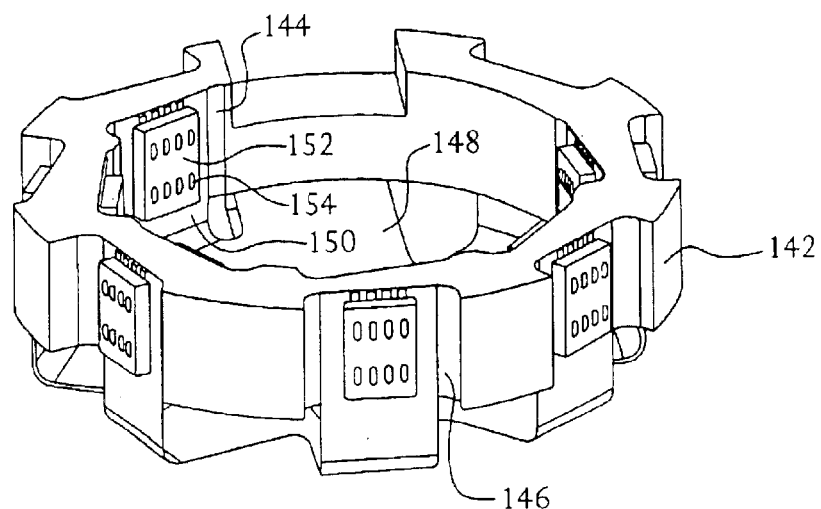
FIG. 4 is a top perspective view of an example of a support ring and flex circuits employed in the emission block shown in FIG. 3.
Figure 5:
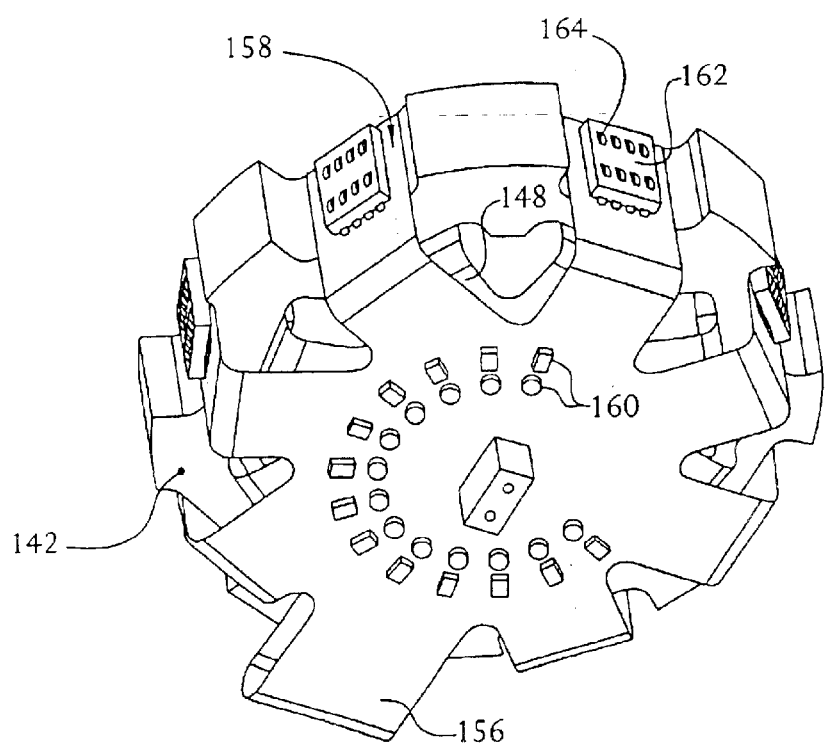
FIG. 5 is a bottom perspective view of the support ring and flex circuits shown in FIG. 4.
Figure 6:
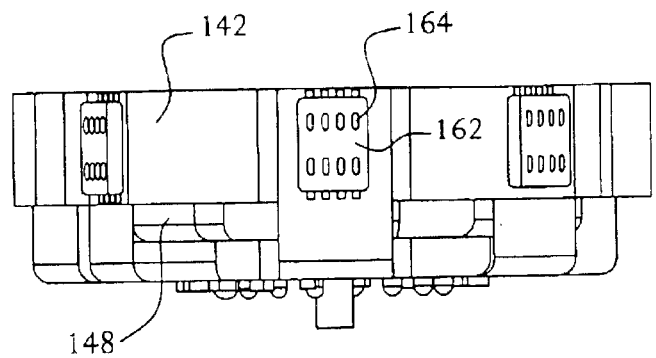
FIG. 6 is a side view of the support ring and flex circuits shown in FIGS. 4 and 5.

As further shown in FIG. 3, for example, emission block 140 include a plurality of detectors 186 which, in this example, are photomultiplier tubes (PMTs). Each photomultiplier tube detector 186 has an opening therein (not shown) which is aligned with a dichroic mirror 176 in its respective mirror assembly 174, and with a filter 182 in its respective filter assembly 180, so that the detector 186 will receive light passing through its respective dichroic mirror 176 and filter 182. Each detector 186 further includes a circuit board assembly 188 that include circuitry for processing the light received by its respective PMT detector 186, as well as power and control circuitry for the PMT, as discussed in more detail below.

Figure 10:
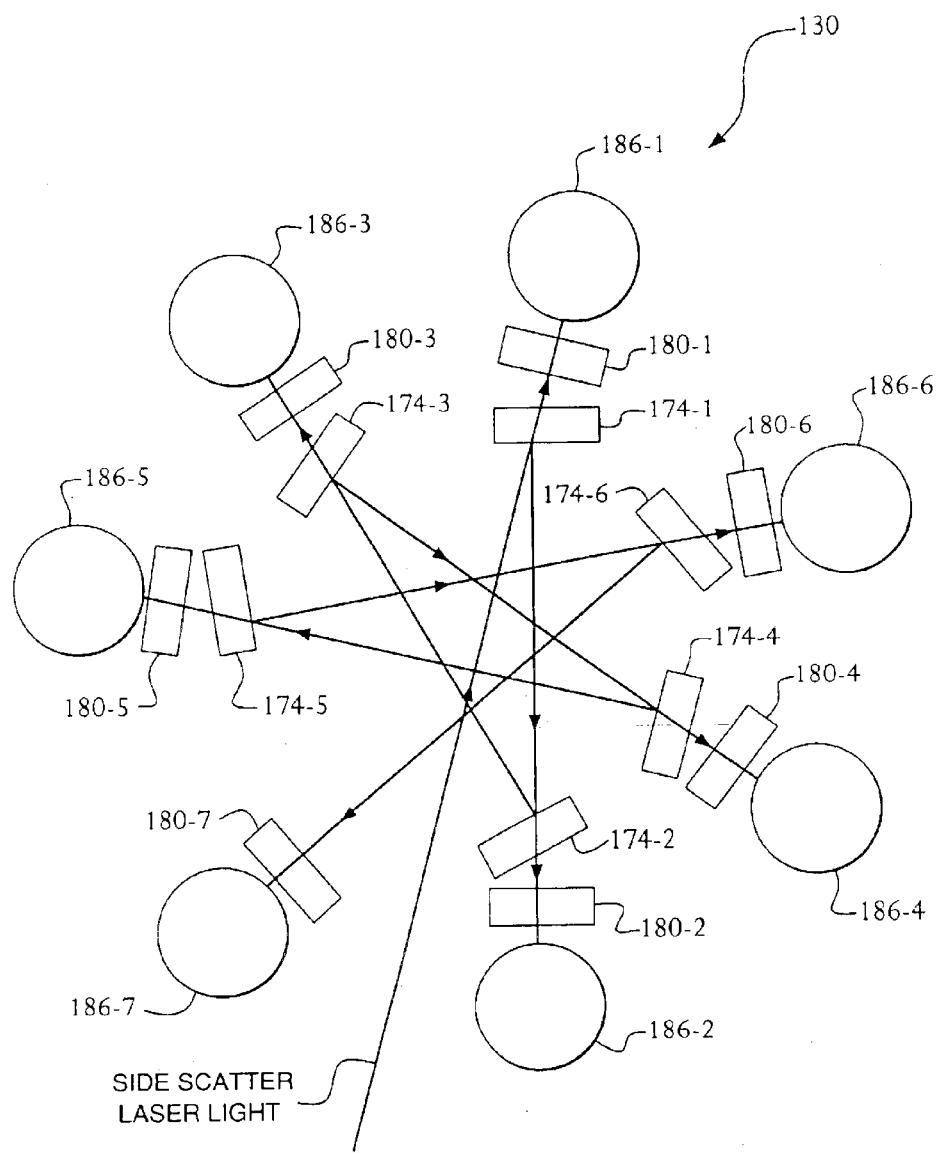
FIG. 10 is a conceptual top view of the emission block shown in FIG. 3 illustrating exemplary paths in which light entering the emission block is reflected and propagates.

As shown in FIG. 3, for example, and in more detail in FIG. 10, the mirror assemblies 174 are angled so that the side-scatter laser light entering the emission block 140 from fiber optic cable 130 is reflected to all of the mirror assemblies 174 and to all of the filter assemblies 180. Specifically, when the laser light enters the emission block 140 from fiber optic cable 130, the laser light propagates to mirror assembly 174-1. The dichroic mirror of mirror assembly 174-1 allows light having a certain wavelength to pass to filter assembly 180-1, which also allows light of that wavelength to be detected by its respective detector 186-1. Detector 186-1 outputs a signal representative of the detected light, which is processed as described in more detail below.

As further illustrated, the portion of the laser light reflected by mirror assembly 174-1 propagates to mirror assembly 174-2, which functions in a manner similar to mirror assembly 174. That is, the dichroic mirror of mirror assembly 174-2 allows light of a certain wavelength (e.g., green light) to pass to filter assembly 180-2 while reflecting light of all other wavelengths. Accordingly, the light passing to filter assembly 180-2 will pass through the filter of filter assembly 180-2 and be received by detector 186-2, while the reflected light will propagate to mirror assembly 174-3. As can be appreciated from the above description, mirror assemblies 174-3 through 174-6 will each allow light within a certain respective wavelength range to pass through to the corresponding filter assemblies 180-3 through 180-6, respectively, while reflecting light of all remaining wavelengths. It is noted that the light reflected by mirror assembly 174-6 will propagate directly into filter assembly 180-7, because no further reflection is necessary. Filter assembly 180-7 will therefore allow light within a respective wavelength to pass to its corresponding detector 186-7.

As discussed above, each laser 122 (see FIG. 1) of the flow cytometer 100 is associated with a respective fiber optic cable 130 and emission block 140. Accordingly, as discussed in more detail below, if flow cytometer 100 includes, for example, four different lasers 122, then the flow cytometer will also include four emission blocks 140, with each emission block 140 being associated with a respective laser 122 to receive side-scatter laser light in the manner described above.

Figure 11:
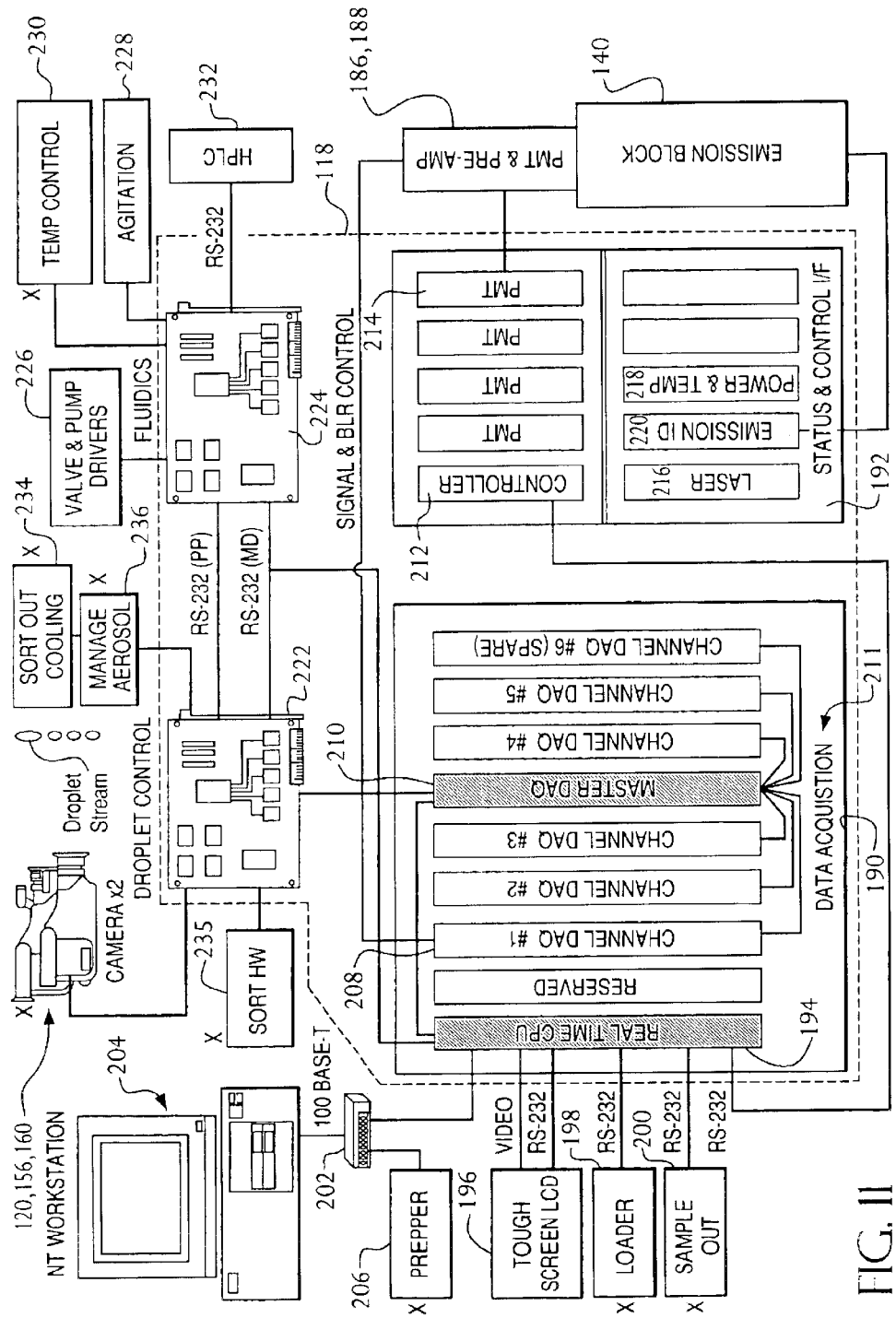
FIG. 11 is a block diagram illustrating an example of the electronic components employed in the flow cytometer shown in FIGS. 1 and 2 according to an embodiment of the present invention.

An example of the electronics included in the flow cytometer 100 is shown in block diagram format in FIG. 11. As discussed above, the flow cytometer 100 includes a controller 118 which, in this example, includes a data acquisition unit 190, a status and control unit 192, a droplet control module 222 and a fluidics control module 224. As indicated, the data acquisition unit 190 includes a processor 194 which, in this example, is a real-time or near real-time CPU, such as a Pentium III processor or any other suitable processor. The processor 194 is coupled to the screen LCD 196 of the flow cytometer 100, as well as a sample loader 198 and sample output device 200. The processor 194 is further coupled to a hub 202 which provides data to and from work station 204 and processor 194 as described in more detail below. It is noted that the processor 194 provides the data pertaining to the event readings to the work station 204 in packet format in real-time or near real-time. The hub 202 further provides data to and from processor 194 and a prepper unit 206 which can be, for example, any type of sample preparation unit such as that described in U.S. patent application Ser. No. 09/447,804, referenced above.

The data acquisition unit 190 further include a plurality of data acquisition modules 208 that are each capable of acquiring data from respective circuit board assemblies 188 of the detectors 186 discussed above as described in more detail below. The data acquisition unit 190 further includes a master data acquisition module 210 that gathers the data from all of the other data acquisition modules 208 via a plurality of link-ports 211 and provides the data to processor 194 as discussed in more detail below.

As further illustrated, the processor 194 of data acquisition unit 190 communicates with the controller 212 of status and control unit 192 to control, for example, the fluid flow, drop delay, PMT driving voltage, and so on as described in more detail below. The status and control unit 192 include PMT modules 214 which, under the control of controller 212, control the driving voltage of the PMT detectors 186 as discussed in more detail below. The status and control unit 192 further include a laser control module 216 which, under control of controller 212, controls operation of laser 122.

The status and control unit 192 also includes a power and temperature control module 218 that controls, for example, the power to components of the flow cytometer 100, as well as the temperature of the sheath and sample fluid.

In addition, status and control unit 192 further includes an emission identification (ID) module 220 that receives information from the first flex circuit 148 and second flex circuit 156 indicative of the locations of the mirror assemblies 174 and filter assemblies 180, in the emission block 140. That is, as discussed above, each mirror assembly 174 and filter assembly 180 includes a memory in which is stored information pertaining to its respective mirror or filter. The circuitry in the first flex circuit 148 is capable of accessing the memory in the filter assemblies 180, and providing the content of this memory to the emission ID module 220. Likewise, the circuitry in the second flex circuit 156 is capable of accessing the memories in the filter assemblies 180 and providing that information to the emission ID module 220. The emission ID module 220 then can determine whether each of the mirror assemblies 174 and filter assemblies 180 are in the appropriate positions based on information pertaining to a desired configuration stored in a memory that was provided, for example, by work station 204. If the emission ID module 220 determines that a mirror assembly 174 or filter assembly 180 is missing or in an incorrect location in the emission block 140, or if an erroneous or faulty mirror assembly 174 or filter assembly 180 has been installed in the emission block 140, emission ID module 220 will provide the appropriate data to, for example, the controller 212, which can then provide the data to the processor 194. The processor 194 can then provide this data to, for example, work station 204, which can display an appropriate error message. This error message can indicate the location of the incorrect mirror or filter assembly in the emission block 140, and the work station 204 can also display the filter and mirror configuration, which therefore greatly simplifies troubleshooting.

As further shown in FIG. 11, the master data acquisition module 210, which is described in more detail below, receives from the data acquisition modules 208 event data that has been provided to the data acquisition modules 208 from the PMT detectors 186 of the emission blocks 140. Prior to running the flow cytometer 100 to detect events, the work station 204 can download data via the hub 202 and processor 194 to the master data acquisition module 210. This downloaded data is stored in a memory in the master data acquisition module 210 and indicates to the master data acquisition module 210 the channel configuration of the data acquisition modules 208, so that the master data acquisition module 210 can recognize which channels of the data acquisition modules 208 are active, and the type of data (e.g., representative of side scatter blue light, side scatter red light and so on) that the data from each channel represents, as discussed in more detail below.

The master data acquisition module 210 further provides and receives data to and from the droplet control module 222 and the fluidics control module 224 to control the operation of the flow cytometer 100 in the manner described above. For example, the master data acquisition module 210 can receive high-speed clock data from the droplet control module 222 that gives the master data acquisition module 210 a time reference as to the rate of drop formation (e.g., 50 thousand drops per second). Master data acquisition module 210 can use this time base to synchronize a direction command signal which can be, for example, a four bit binary code, that the master data acquisition module 210 sends to the droplet control module 222 so that the droplet control module 222 can control the charging unit 147 (see FIG. 2) as appropriate to achieve the desired charging of the appropriate droplets containing a cell or particle of interest. By charging the droplet with the appropriate charge, the droplet control module 222 thus controls the amount and direction of deflection that the deflection plates 1142 and 1144 (see FIG. 2) deflect the charged droplet. The deflection plates 1142 and 1144 are included among the sorting hardware 235 shown in FIG. 11. The droplet can be deflected, for example, to be received in one of any suitable number (e.g., sixteen) collection vessels 1142, 1146 and 1150.

In addition, the master data acquisition module 210 can receive data from the processor 194 that has been acquired by, for example, detectors 120, 1156 and 1160 that provide information concerning the status of the break-off point 112 (see FIG. 1) as well as information pertaining to the droplet sorting. Based on this data, the master data acquisition module 210 can provide control signal to the droplet control module 222 to control, for example, drop delay, droplet formation and so on as discussed above with regard to FIGS. 1 and 2, processor 194 can further control the droplet control module 222 to control, for example, a cooling module 234 and an aerosol management module 236 to control the temperature of the sorted sample, for example, as well as to control sorting and aerosol containment management and safety devices in the flow cytometer 100. It is also noted that the fluidics control module 224 can control the valve and pump drivers 226, the agitation module 228, the temperature control module 230 and the multiport valve HPLC 232 to control the temperature of the fluid sample and sheath fluids, to agitate the sample in the sample reservoir 106 (see FIG. 1), and to control the flow of fluids in the flow cytometer 100.

Figure 12:
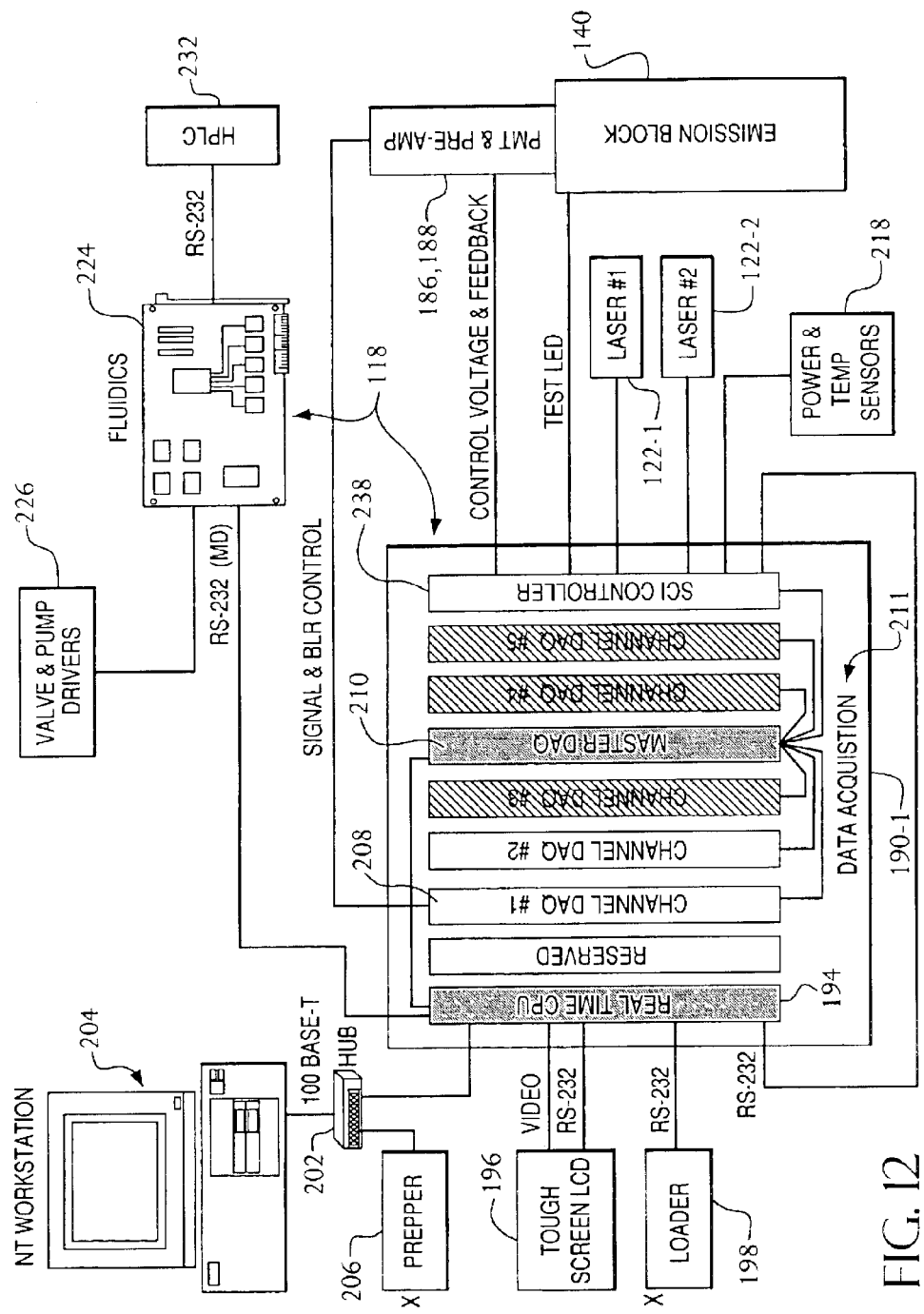
FIG. 12 is a block diagram illustrating anther example of the electronic components employed in the flow cytometer shown in FIGS. 1 and 2 according to another embodiment of the present invention.
Figure 13:
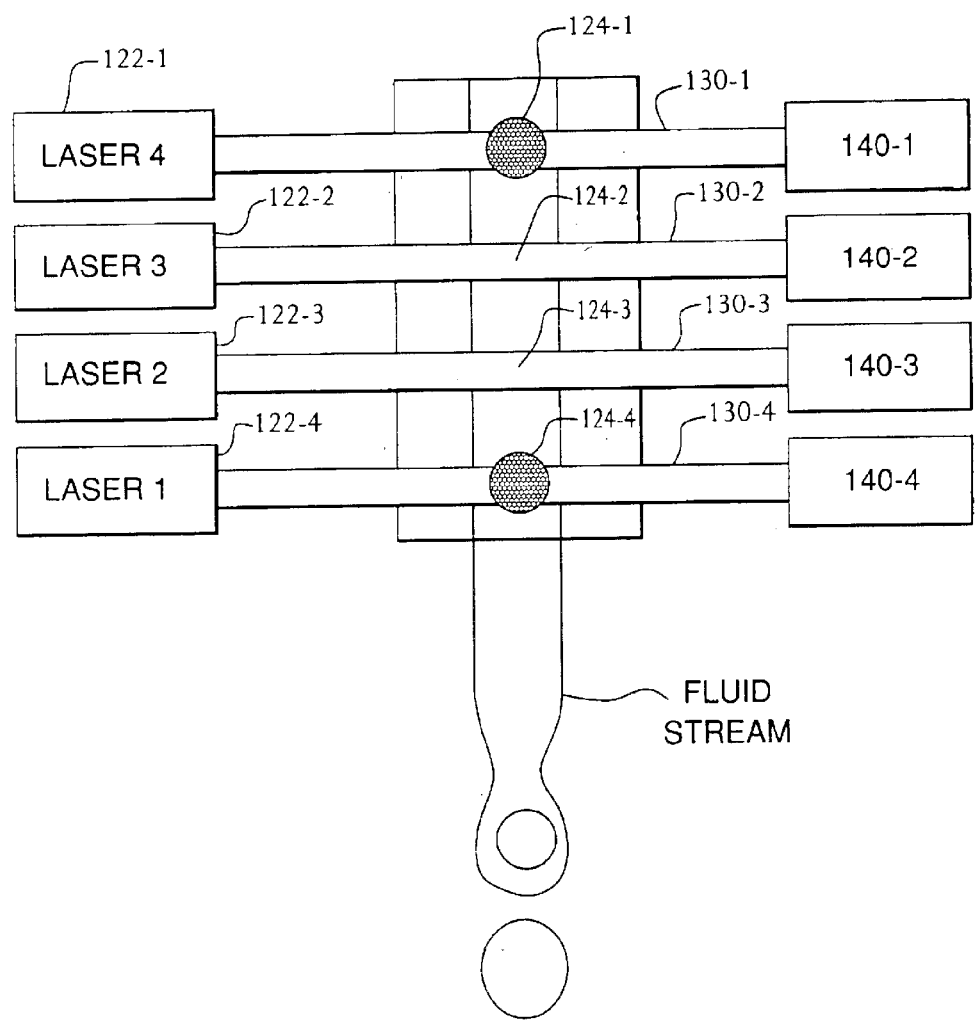
FIGS. 13–16 are conceptual illustrations of an exemplary relationship between multiple lasers and multiple emission blocks in the flow cytometer shown in FIGS. 1 and 2 according to an embodiment of the present invention.
Figure 14:
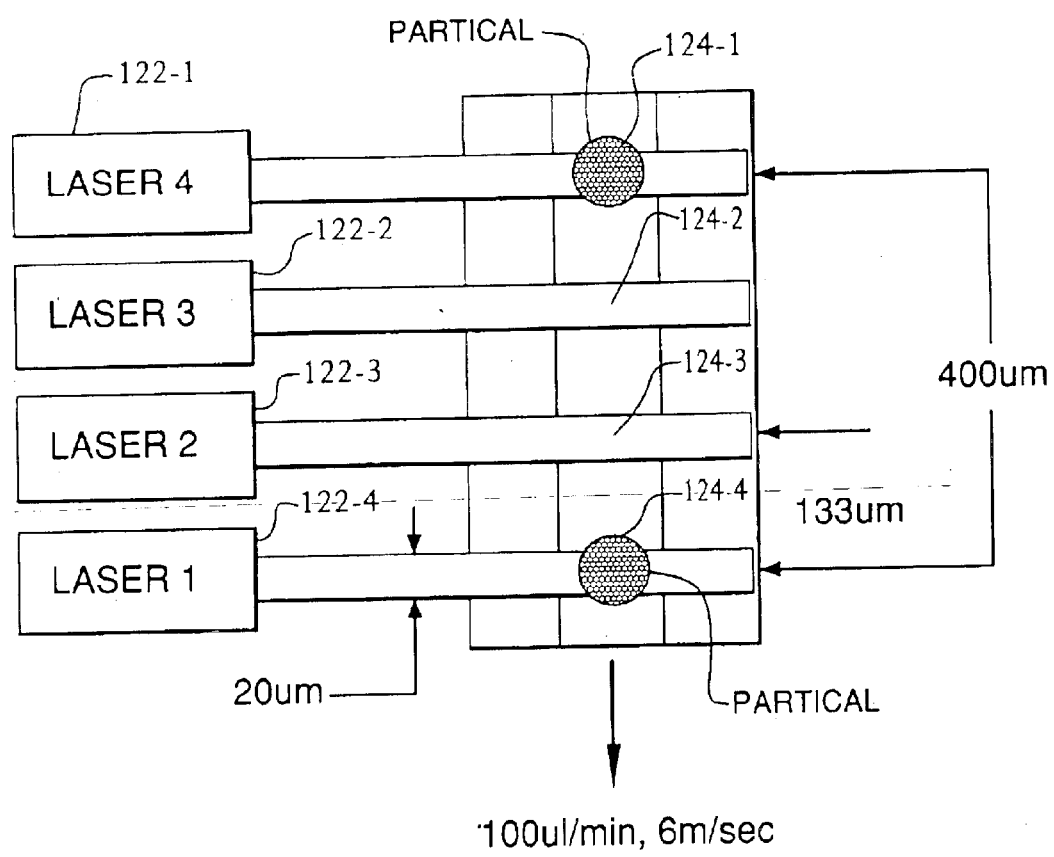

It is further noted that the flow cytometer 100 need not include all of the electronics shown in FIG. 11. For example, if the flow cytometer 100 is not equipped to perform droplet sorting, certain components shown in FIG. 11 can be omitted. As shown in FIG. 12, the hardware of the data acquisition unit 190 and status and control unit 192 can consolidated into a data acquisition unit 190-1. The components of the data acquisition unit 190-1, such as the processor 194, data acquisition modules 204 and master data acquisition module 210 operate in a manner similar to those described above with regard to FIG. 11. However, the data acquisition module 190-1 includes an SCI controller 238 which performs the operations performed by status and control I/F unit 192 shown in FIG. 11, such as controlling the driving voltages of the lasers 122 and power and temperature sensor module 218 which operates as described above. The SCI controller 238 further controls operation of the driving voltage of detectors 186 in a manner described below, and receives and processes the mirror and filter assembly position information received from the emission block 140 in a manner similar to the emission ID module 220 described above.

The operation of the above components in relation to the operation of flow cytometer 100 will now be described. As discussed above, flow cytometer 100 will typically employ more than one laser 122 to sample more than one type of cell or particle of interest, or more than one characteristic of a cell or particle of interest. The following discussion will assume that the flow cytometer 100 includes four lasers 122, each emitting light having a different wavelength.

Figure 15:
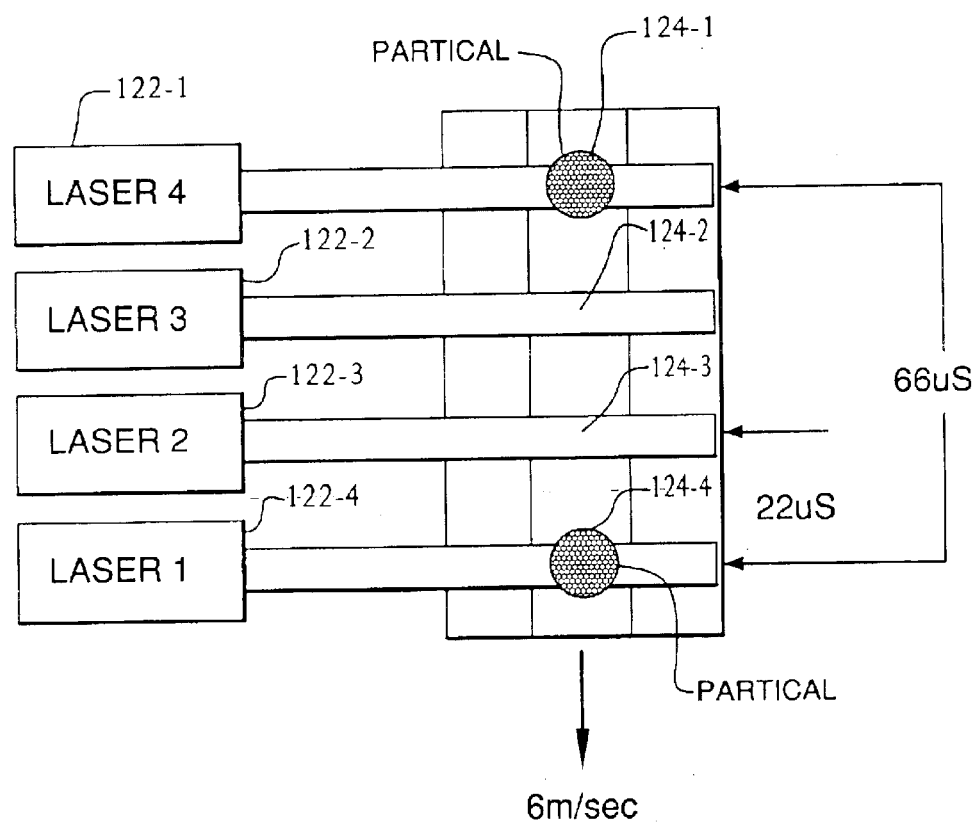
Figure 16:
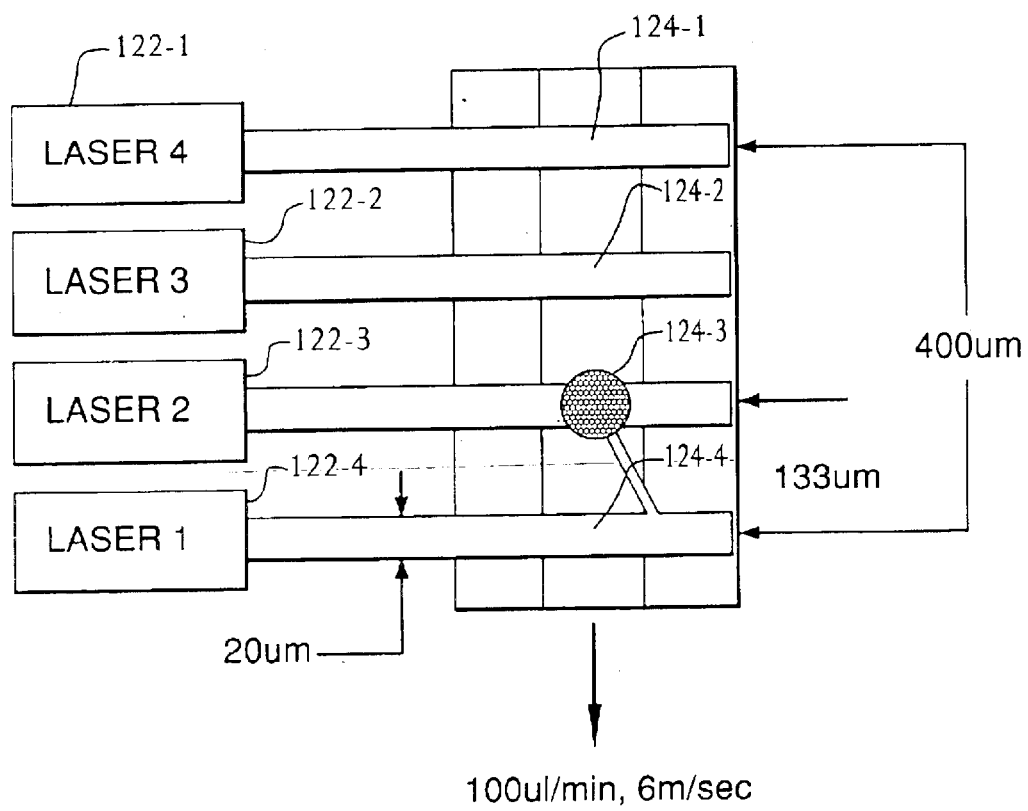
Figure 17:
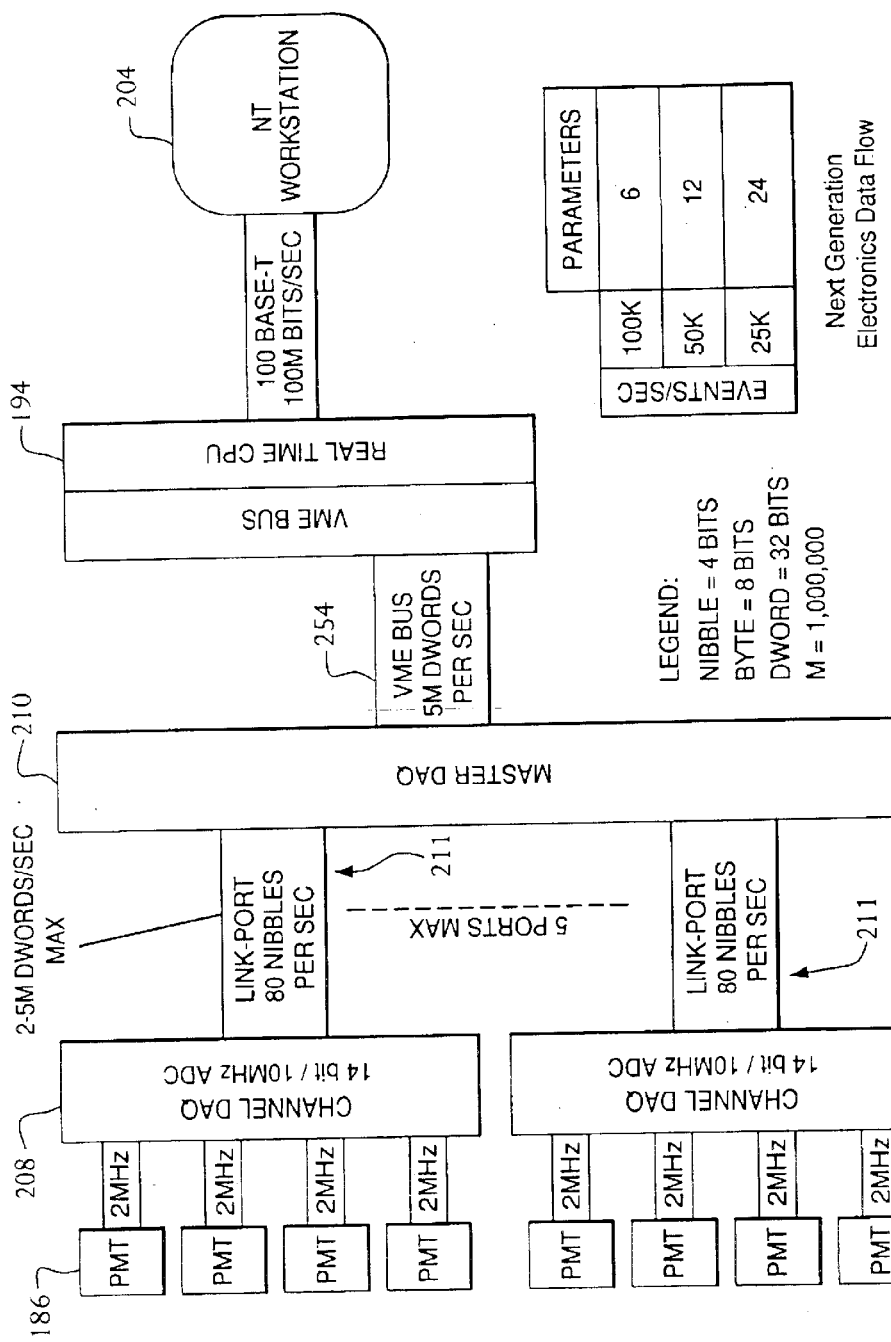
FIGS. 17–20 are conceptual block diagrams showing exemplary relationship between certain components shown in FIGS. 11 and 12.

As discussed above and as shown conceptually in FIGS. 13–16, if the flow cytometer 100 includes four lasers 122-1 through 122-4, then the flow cytometer 100 will include four corresponding fiber optic cables 130-1 through 130-4 that feed the respective side-scatter laser lights to the respective emission blocks 1401 through 140-4. As further shown, the laser light emitted from these respective lasers 122-1 through 122-4 strike respective interrogation points 124-1 through 124-4 on the fluid stream. In this example, the interrogation points are displaced by about 133 micrometers along the direction of flow of the fluid stream, which translates into a spacing of about 22 microseconds for a fluid stream flowing at a rate of 6 meters per second. As shown in FIG. 16, this spacing also permits inter-laser mixing to occur. For example, the side scatter laser light from interrogation point 124-3 can enter the fiber optic cable 130-4 dedicated to receive side scatter laser light from interrogation point 124-4. The mirror assemblies 174 and filter assemblies 180 in the emission blocks 140-1 through 140-4 can be configured to eliminate any light of undesired wavelengths as discussed above, in the event that unwanted inter-laser mixing occurs.

Further details of the relationship between the detectors 186, a data acquisition module 208, master data acquisition module 210, processor 194 (real time CPU) and the work station will now be described with regard to FIGS. 17–21. In this arrangement, each data acquisition module 208 can receive data from four detectors 186 from any of the emission blocks 140. For purposes of this discussion, data acquisition module 208 is configured to receive side scatter laser light that has been generated by the four different wavelength lasers 122-1 through 122-4.

Figure 18:
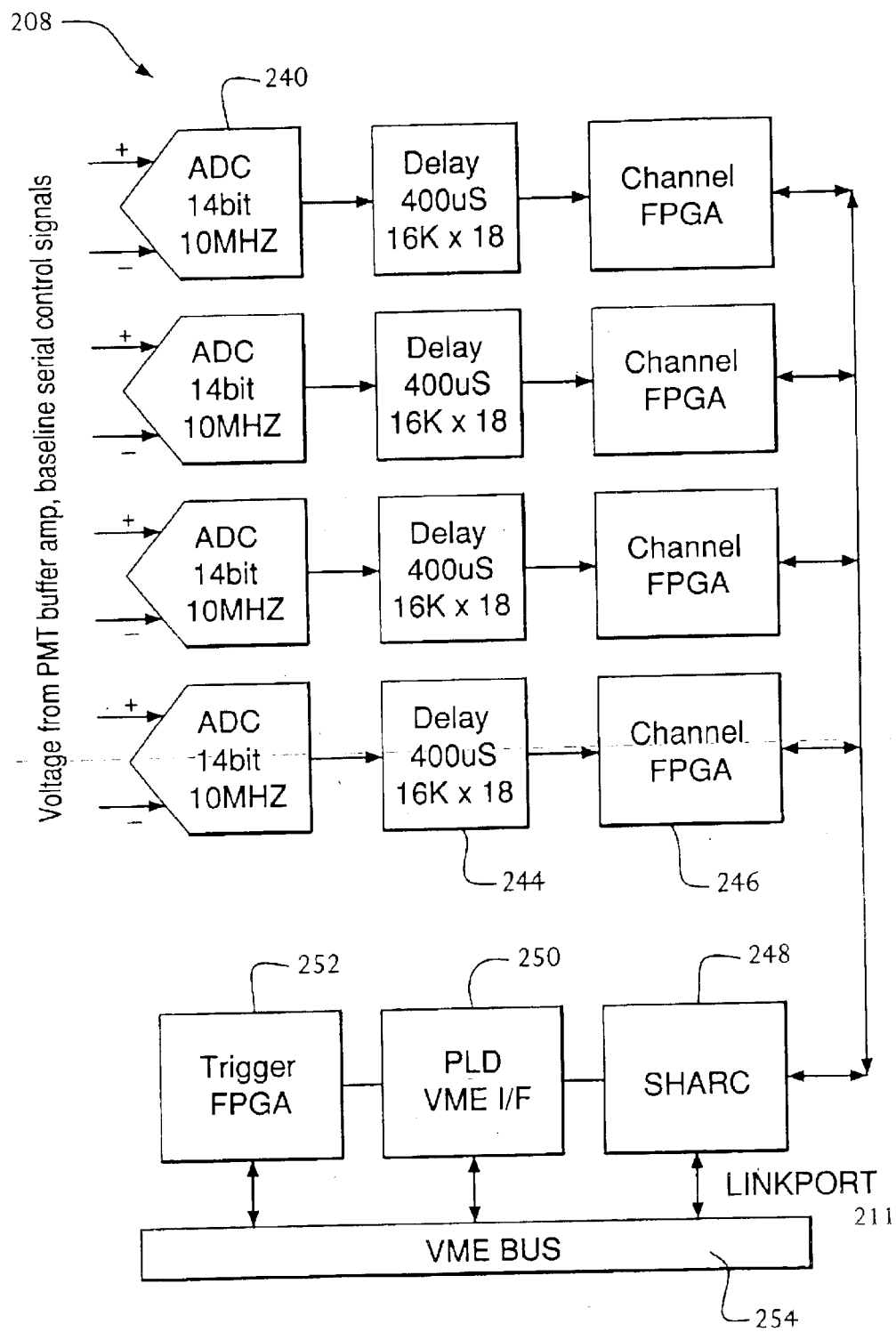
Figure 19:
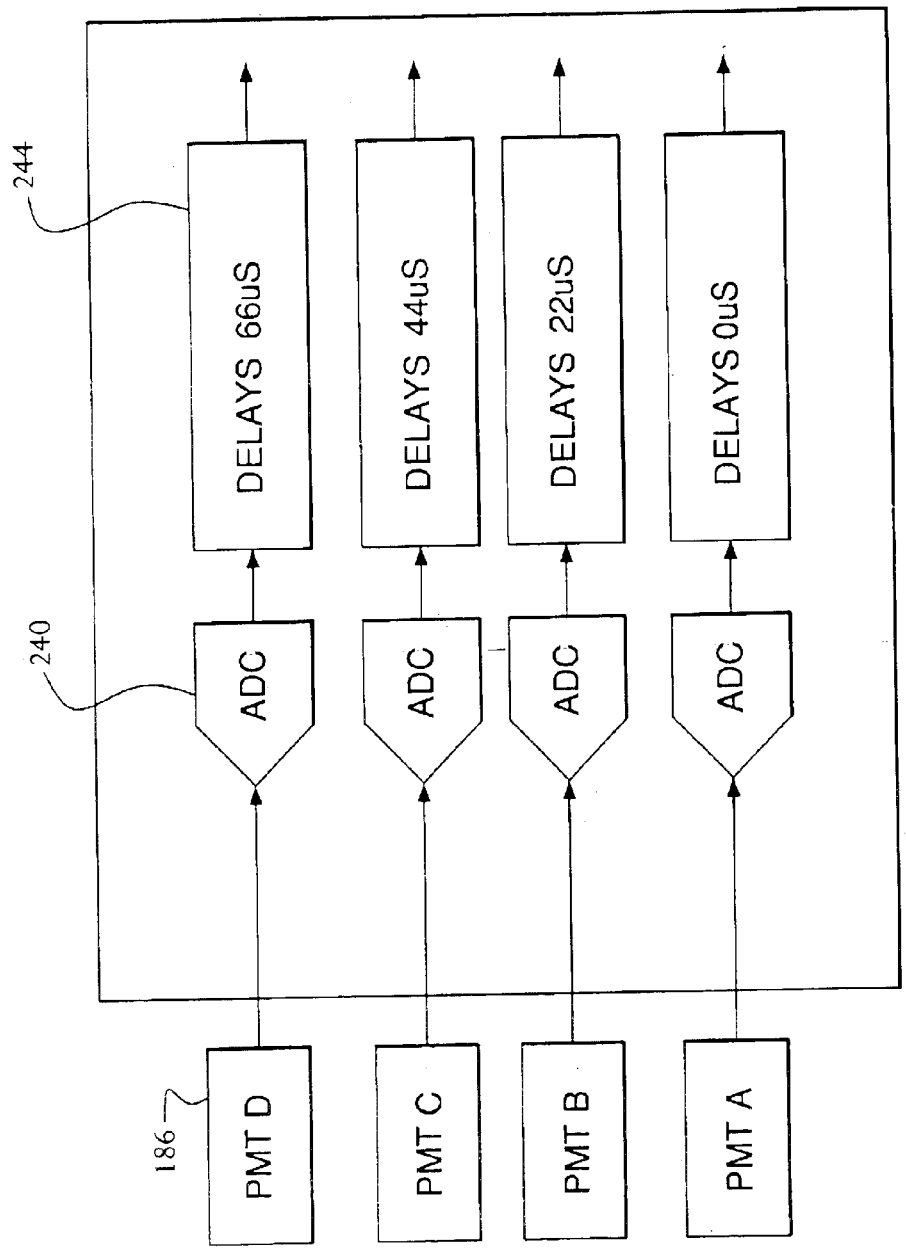
Figure 21:
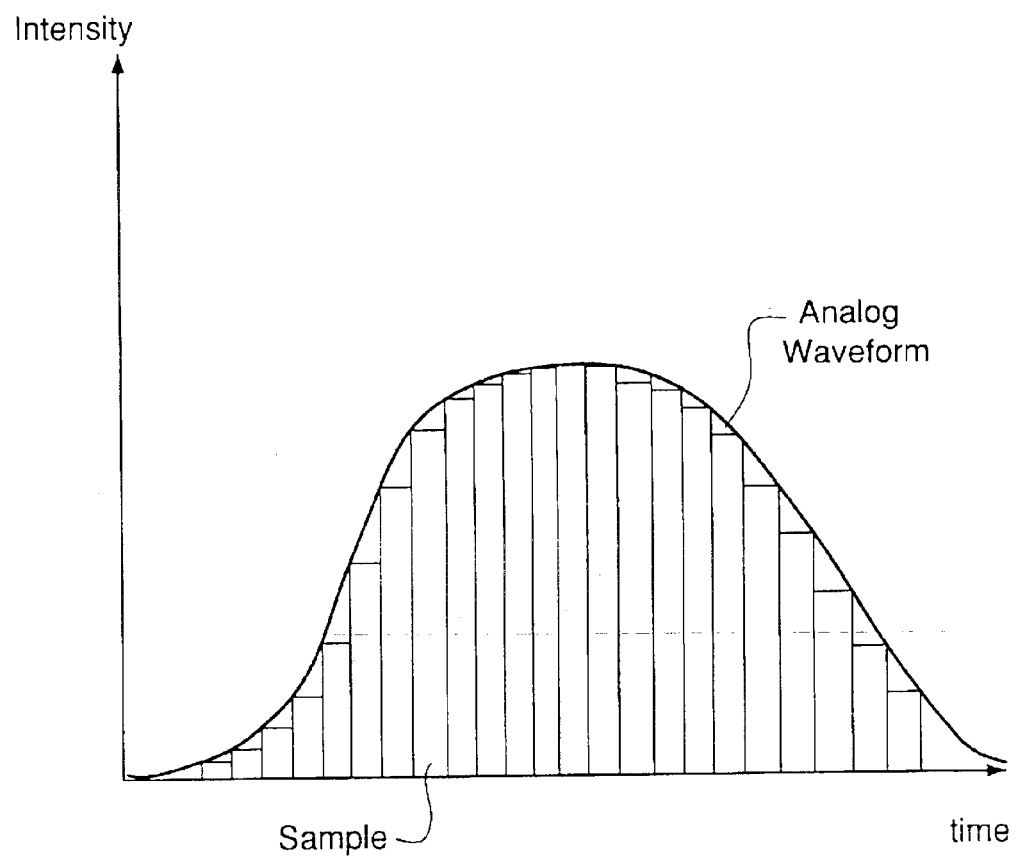
FIG. 21 illustrates an example of a waveform as captured and sampled by the circuitry shown in FIGS. 11 and 12.

As illustrated, the analog data signals from the detectors 186 are input to their respective data acquisition module 208 as 2 MHz bandwidth (BW) analog signals. Further details of the data acquisition module are shown in FIGS. 18 and 19. That is, the signal from each detector 186 is input to a respective analog-to-digital (A/D) converter 240 where the analog data is converted into digital data. As illustrated, each A/D converter 240 have differential inputs to maximize common mode rejection of the received analog signals. The frequency (e.g., 10 MHz) at which the A/D converters 240 are operating enable the A/D converters 240 to take multiple samples (e.g., 10 or 20, or more) of the waveform as shown in FIG. 21 in real-time or near real-time. As indicated, the intensity of the signal will typically increase to a maximum when the particle or cell of interest is at the center of the interrogation point, and then drop-off to a minimum as the cell passes out of the interrogation point 124. Accordingly, each individual sample of the waveform will have a value representing the characteristic (e.g., height) of that sampled portion of the waveform. This sampling of the entire or substantially the entire waveform improves the details at which the waveforms can be analyzed and compared, for example, to other waveforms representative of other events. Accordingly, this sampling allows for a more detailed sampling of the characteristics of each event.

The digital data output by each A/D converter 240 is provided to a respective delay circuit 244 which imposes a respective delay on the digital data as described in more detail below. As shown, for example, in FIG. 19, the delay imposed by each delay circuit 244 is set to compensate for the delays between the interrogation points 124-1 and 124-4 as shown in FIG. 15 or, in other words, to compensate for the time delay that occurs between when the side scatter light representative of a particle or cell of interest at interrogation point 124-1 is received by a detector 186 in emission block 140-1 and when the side scatter light representative of that particle or cell of interest reaching interrogation points 124-2 through 124-4 are subsequently received by detectors 186 in their respective emission blocks 140-2 through 140-4.

The digital data from each delay circuit 244 is provided to a respective channel field programmable gate array (FPGA) circuit 246, which provide the data to a Super Harvard Architecture Computer (SHARC) unit 248. It is noted that each channel FPGA circuit 246 can process the characteristics of the data samples to produce data representing a single characteristic of the analog waveform, such as the width or height of the waveform, if desired, instead of passing all of the samples (e.g., 20 samples per waveform as discussed above) to the SHARC unit 248. Also, the channel FPGA circuits 246 will add a time stamp to their respective data prior to passing the data to the SHARC 248. Under the control of a programmable logic device, versa-module Eurocard interface (PLD VME I/F) unit 250 and a trigger FPGA unit 252, the SHARC unit 248 provides the digital data via a link port 211 to the master data acquisition module 210 as indicated.

Specifically, prior to running the flow cytometer 100 to detect the events, the workstation 204 can download channel data to the trigger FPGA unit 252 of each data acquisition module 208 via the hub 202 and processor 194. This channel data indicates to the channel FPGA circuits 246 whether they should collect the data from their respective delay circuits 244, that is, whether they are receiving data on an active channel. The channel data further indicates to the trigger FPGA unit 252 when the trigger FPGA unit 252 should trigger the SHARC 248 to transfer the event data received in parallel from the channel FPGAs 246 to the master data acquisition module 210 via the link port 211.

Figure 20:
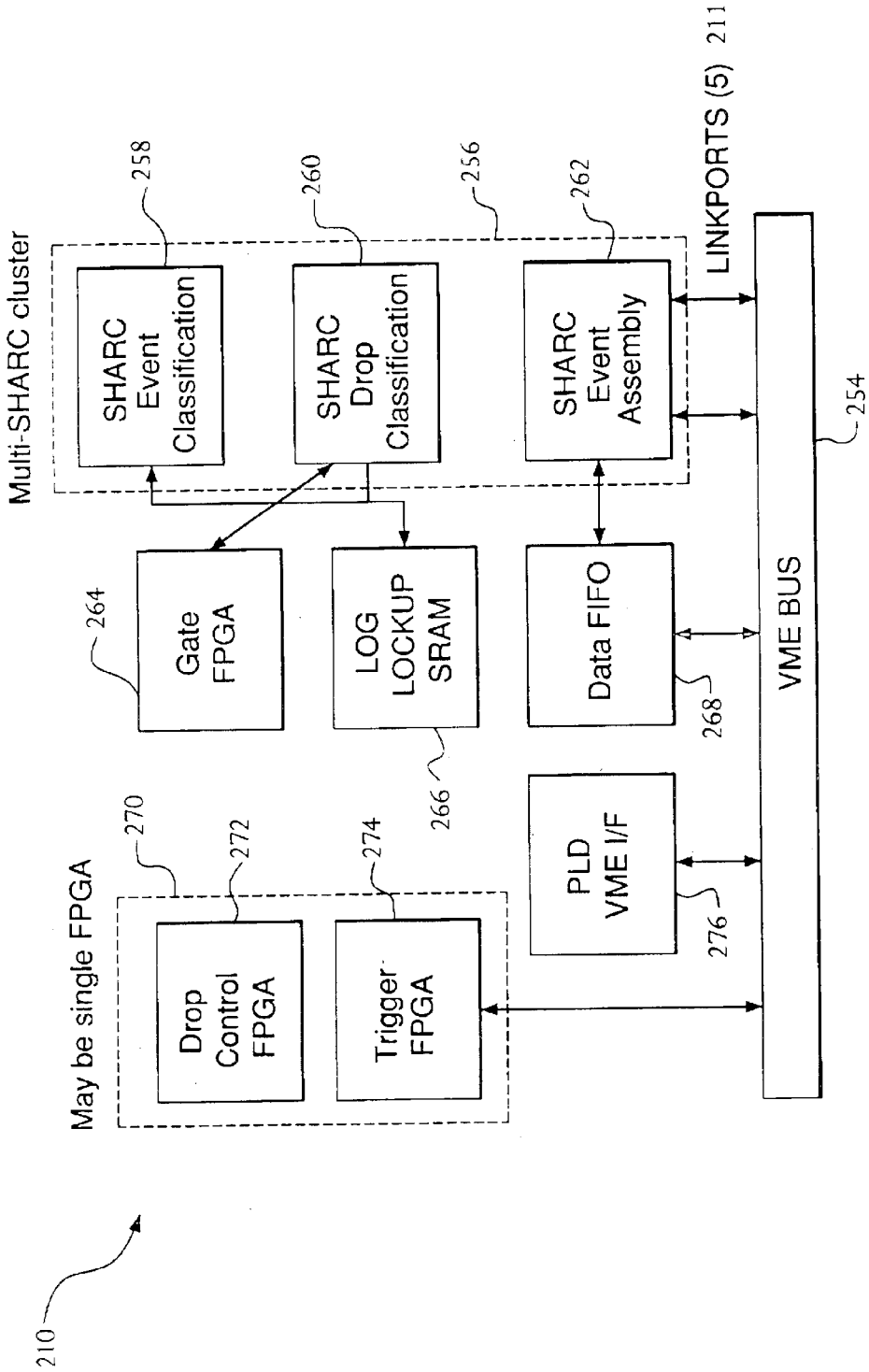

Details of the master data acquisition data module 210 are shown FIG. 20. That is, the master data acquisition module 210 includes a multi-SHARC unit 256 that includes a SHARC event classification unit 258, a SHARC drop classification unit 260 and a SHARC event assembly unit 262, the details of which are described below. The master data acquisition module 210 further include a gate FPGA 264, a logarithmic look-up table 266, and a data FIFO unit 268. Furthermore, the master data acquisition data module 210 includes an FPGA module 270 that includes a drop control FPGA 272 and a trigger FPGA 274. The master data acquisition module further include a PLD VME I/F 276. The details of these components are described below.

Specifically, prior to running the flow cytometer 100 to detect the events, the workstation 204 can download channel data to the trigger FPGA unit 274 of master data acquisition module 210 via the hub 202 and processor 194. This channel data indicates to the trigger FPGA units 252 of each data acquisition module 208 whether they should trigger their respective SHARC 248 to transfer the event data received in parallel from the channel FPGAs 246 to the master data acquisition module 210 via their respective link port 211. That is, when the trigger FPGA units 252 provide their respective indications to the trigger FPGA unit 274 indicating that event data has been received on their appropriate respective channels, the trigger FPGA unit 274 will signal the trigger FPGA units 252 to trigger their respective SHARCs 248 to transfer the event data received in parallel from the channel FPGAs 246 to the master data acquisition module 210 via the link port 211.

When the master data acquisition module 210 receives the event data via the linkports 211, the event data is input to the SHARC event assembly 262. The SHARC event assembly 262 assembles the data into lists, tables or buffers based on their time-stamp that has been added by the channel FPGAs 246. That is, the SHARC event assembly 262 uses the time stamps to determine which data is associated with which event.

If no sorting of cells is to be performed, the SHARC event assembly 262 passes the lists, tables or buffers of data to the data FIFO unit 268. The data FIFO unit 268 sends the lists, tables or buffers of the data via the VME bus 254 to the processor 194. The processor 194 can then provide the data to the work station 204 for further display in, for example, a scatter plot diagram, a graphical representation, and so on.

However, if cell sorting is to be performed, data received by the SHARC event assembly unit 262 is processed by the SHARC event classification unit 258 and SHARC drop classification unit 260. For example, the flow cytometer 100 can be run to sample a portion of the cell sample to therefore provide initial sample data to the work station 204 as discussed above. The work station 204 can display the detected events on, for example, a scatter plot which can be reviewed by the operator. The operator can select certain cells of interest to be sorted by selecting, for example, a region on an interactive display screen of the work station 204. The work station 204 can then pass the desired cell sorting data to the master data acquisition module 210 via hub 202 and processor 194. The master data acquisition module 210 stores this cell sorting data in, for example, the logarithmic lookup SRAM 266.

When the operator reactivates the flow cytometer 100 to continue processing the sample, the SHARC event classification unit 258 and SHARC drop classification unit 260 can access the data in the logarithmic lookup SRAM 266 in real-time or near real-time to determine which data received by the SHARC event assembly unit 262 represents cells to be sorted. The SHARC event classification unit 258 and SHARC drop classification unit 260 can then provide signals to the Drop Control FPGA 272 which can provide the appropriate direction command signal to the droplet control module 222 so that the droplet control module 222 can control sorting as discussed above. The SHARC event assembly 262 can then pass the lists, tables or buffers of data to the data FIFO unit 268, which sends the lists, tables or buffers of the data via the VME bus 254 to the processor 194 as discussed above. The processor 194 can then provide the data to the work station 204 in real-time or near real-time for further display in, for example, a scatter plot diagram, a graphical representation, and so on.

Figure 22:
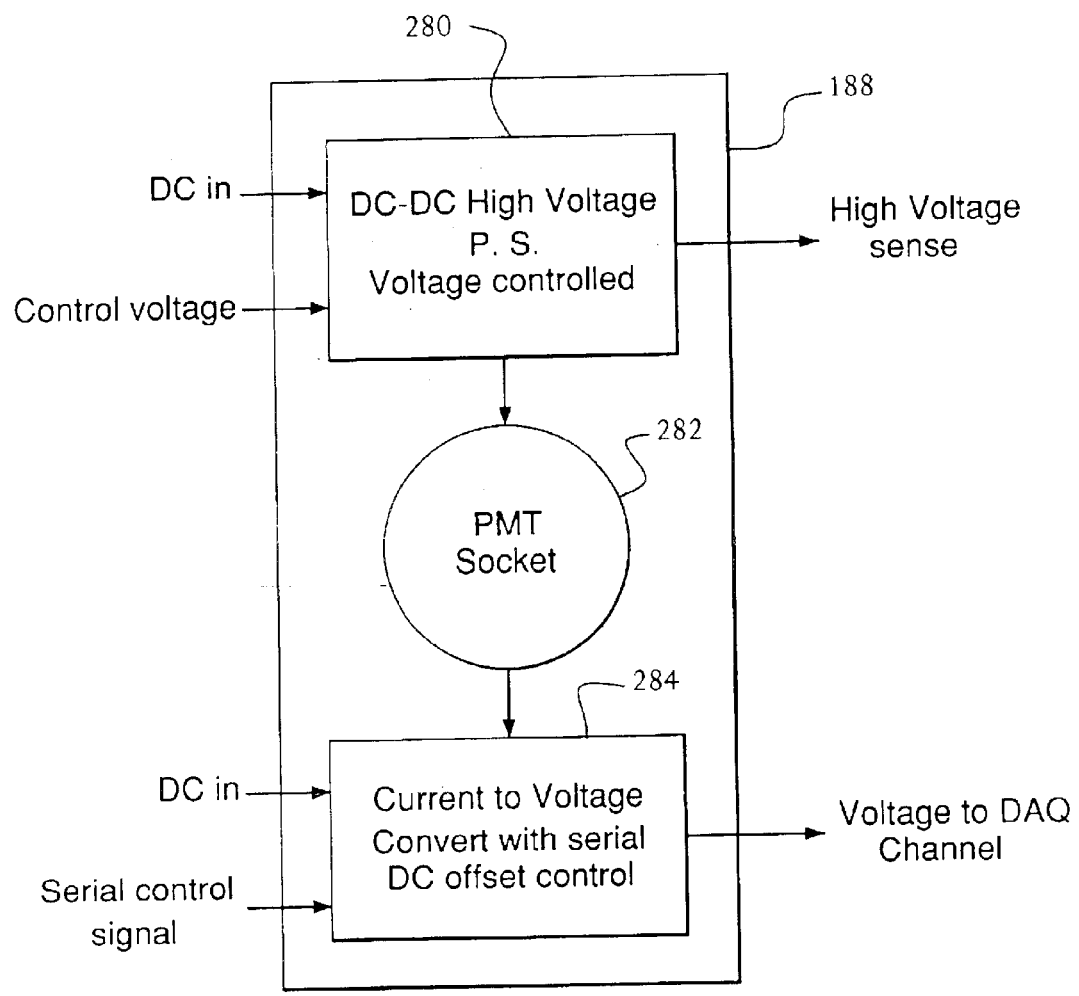
FIG. 22 is a conceptual block diagram of control circuitry for a PMT detector.
Figure 23:
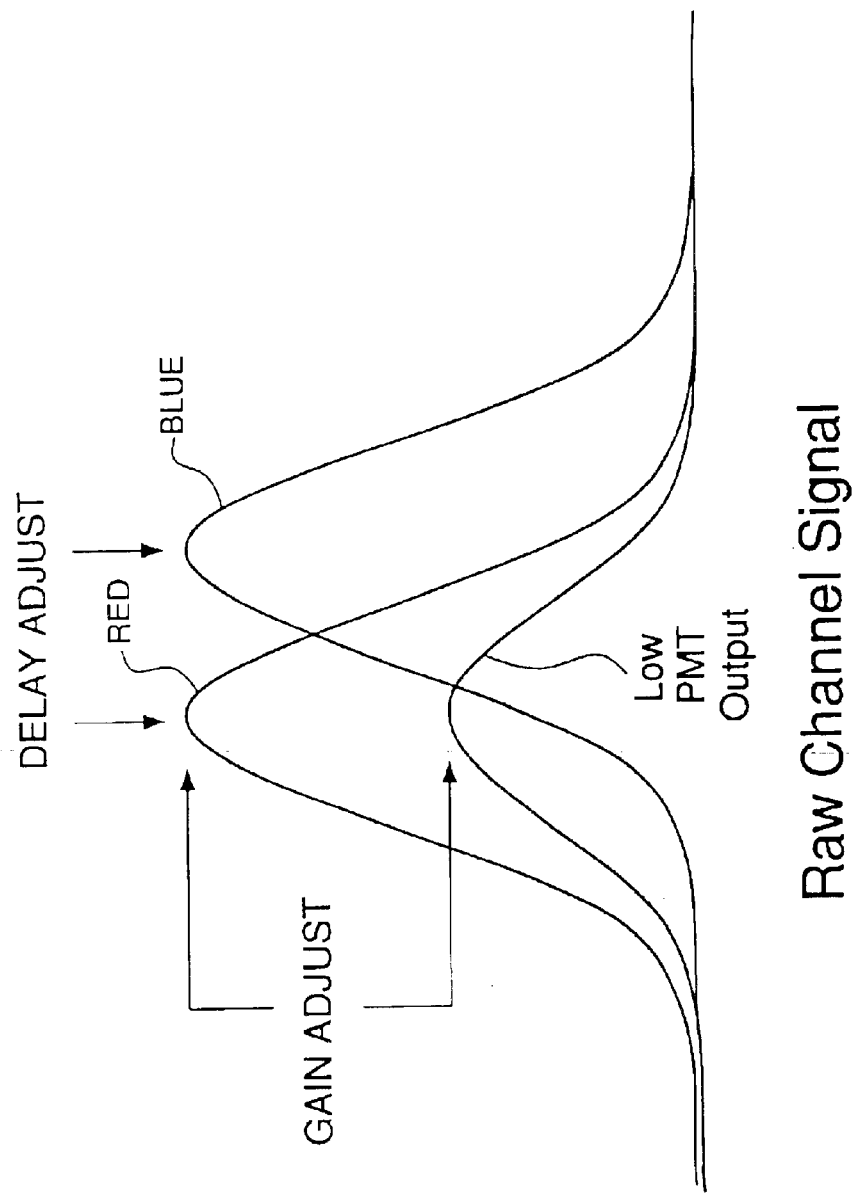

Additionally, the event data can be used to process the sample waveforms in various ways. For example, the above system, in particular, the controller 212 (FIG. 11) or SCI controller 238 (FIG. 12) can adjust system can adjust the voltages applied to the detector 186 (PMTs) to adjust the relative zero point of the PMT detector 186. For example, as shown in FIG. 22, the PMT and circuit board 188 includes a DC high voltage power supply 280 that provide the driving voltage to the PMT socket 282 that drives the PMT. The current from the PMT generated upon, for example, detection of side scatter light as described above is converted by a current voltage converter 284 so that the voltage signal is provided to the respective channel data acquisition module 208 as described above. Voltage control and serial control signal are provided from the PMT controllers 214 in, for example, the respective channel data acquisition module 208 to adjust the base voltage of the PMT, to therefore adjust the relative zero point of the PMT. Accordingly, this adjustment can be used to perform the gain adjustment as shown, for example, in FIG. 23 to increase the height of the smaller waveform to be consistent with the heights of the red and blue waveforms.

Figure 24:
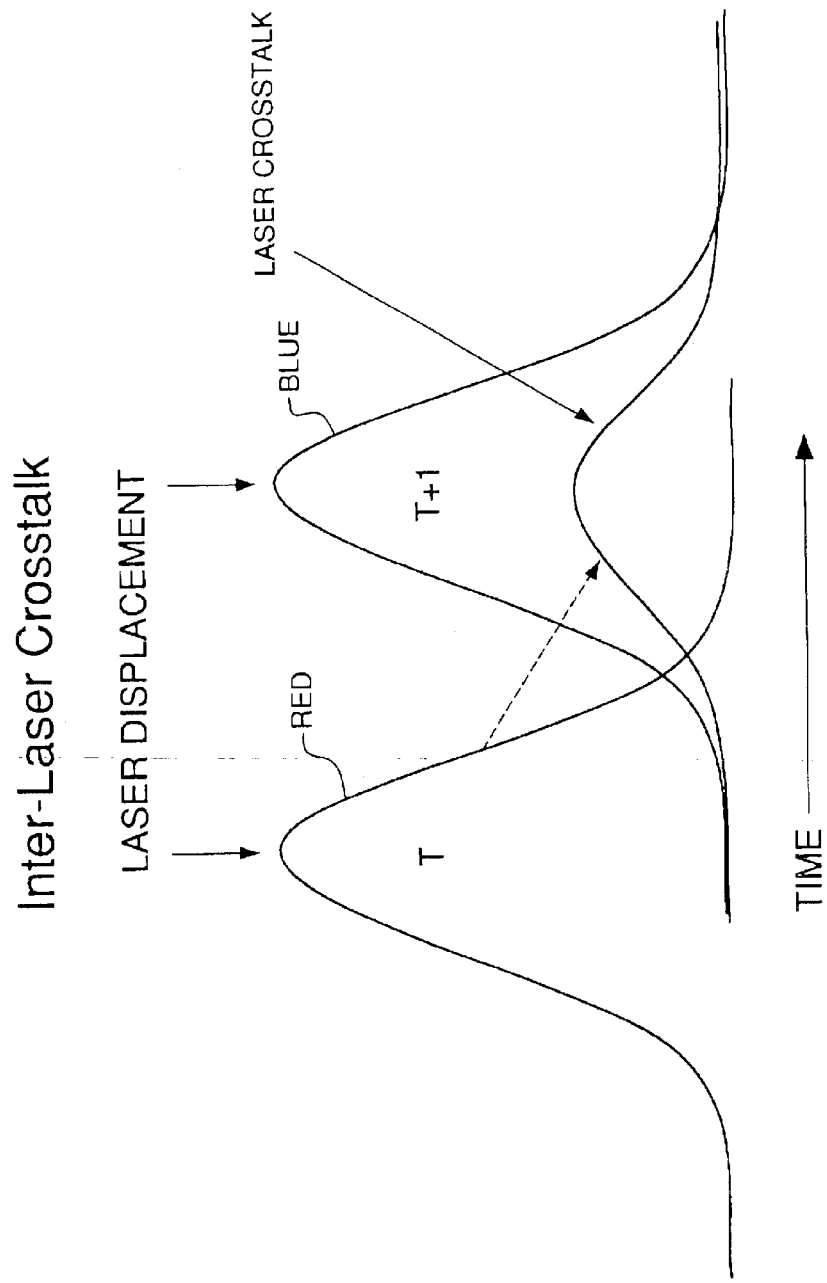
Figure 25:
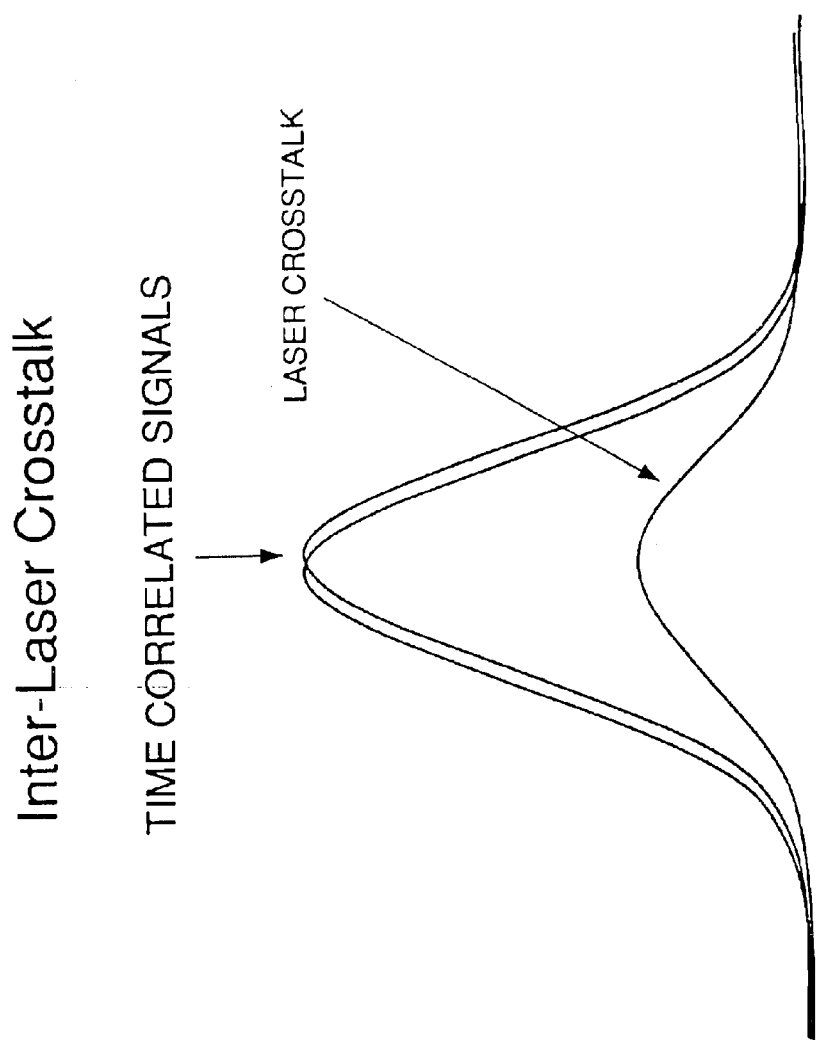
Figure 26:
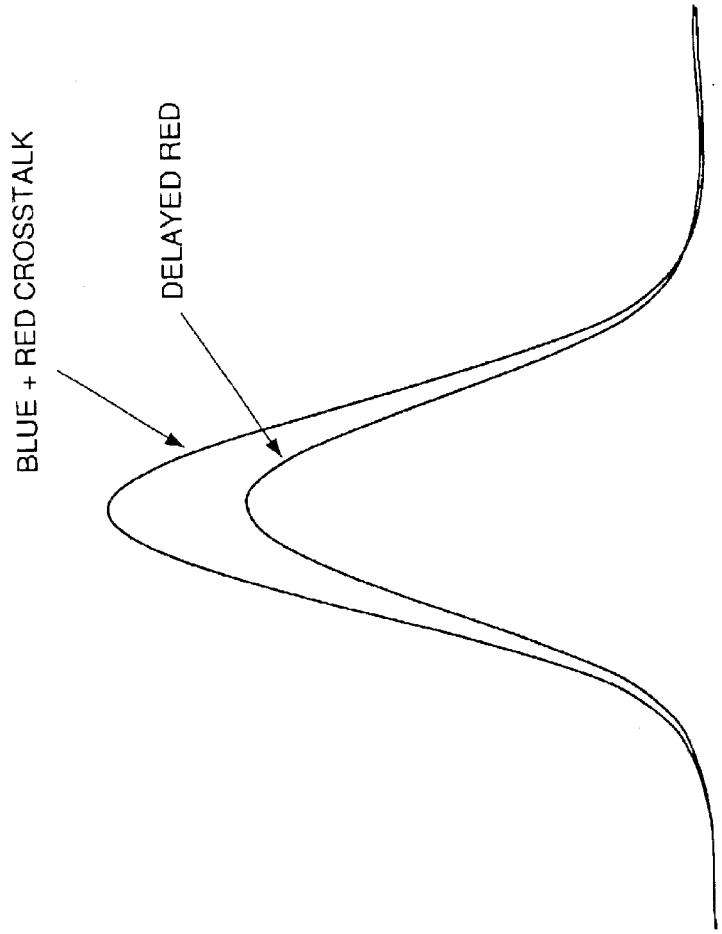

In addition, as shown in FIGS. 24–27, the SHARC event assembly 262 the master data acquisition module 210 can compare the entire sample wave form of data obtained from different detectors 186 and can perform different types of processing functions on this data in a real time or near-real time basis. For example, the event data representative of the red side scatter light signal received at time T can be delayed so that it can be compared with the event data representative of the blue side scatter light signal received at time T+1 as shown in FIG. 24, so that the signals can be time correlated as shown in FIG. 25. Furthermore, as shown in FIGS. 26 and 27, the data signals can be processed to remove crosstalk that can occur as discussed above. In this event, the blue data represented as the "blue+red crosstalk" can be processed to remove a percentage of the red signal that is affecting the magnitude of the blue data, so that the magnitudes of the blue and red data can be made similar for comparison as shown in FIG. 27.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A system for processing at least one signal representative of an event detected by at least one detector in a flow cytometer, the system comprising:

a detector, adapted to detect light emitted from said event in said flow cytometer and to generate a signal representative of said emitted light;

a sampling device, adapted to receive portions of said signal from said detector in time sequence and to generate a respective value representative of the respective magnitude of each respective portion of said signal as said respective portion of said signal is being received; and an arithmetic device, adapted to arithmetically combine a designated value with each of said values.

2. A system as claimed in claim 1, wherein:

said sampling device receives a number of said portions totaling substantially all of said signal, and generates said values which represent said portions of substantially all of said signal.

3. A system as claimed in claim 1, wherein:

said signal is an analog signal representative of a light signal emitted from said event as detected by said detector.

4. A system as claimed in claim 1, wherein:

said arithmetic device includes a subtracter which is adapted to subtract said designated value from each of said values.

5. A system as claimed in claim 1, wherein:

said designated value is representative of an undesired signal detected by said detector.

6. A system as claimed in claim 1, wherein:

said designated value is representative of a characteristic of said detector.

7. A method for processing at least one signal representative of an event detected by at least one detector in a flow cytometer, the method comprising:

generating a signal representative of light emitted from said event in said flow cytometer using a detector;

receiving portions of said signal from said detector in time sequence;

generating a respective value representative of the respective magnitude of each respective portion of said signal as said respective portion of said signal is being received; and arithmetically combining a designated value with each of said values.

8. A method as claimed in claim 7, wherein:

said receiving receives a number of said portions totaling substantially all of said signal.

9. A method as claimed in claim 7, wherein:

said signal is an analog signal representative of a light signal emitted from said event as detected by said detector.

10. A method as claimed in claim 7, wherein:

said arithmetic combining includes subtracting said designated value from each of said values.

11. A method as claimed in clam 7, wherein:

said designated value is representative of an undesired signal detected by said detector.

12. A method as claimed in claim 7, wherein:

said designated value is representative of a characteristic of said detector.

13. A system for processing at least two signals representative of an event detected by at least two detectors in a flow cytometer, the system comprising:

a first detector and a second detector, adapted to detect light emitted from said event in said flow cytometer and to generate a first signal and a second signal representative of said emitted light, respectively;

a sampling device, adapted to receive portions of said first signal from said first detector in time sequence and to generate a respective value representative of the respective magnitude of each respective portion of said first signal as said respective portion of said first signal is being received, and to receive portions of said second signal from said second detector in time sequence and to generate a respective value representative of the respective magnitude of each respective portion of said second signal as said respective portion of said second signal is being received, wherein said sampling device receives said portions of said first signal at a time different form that during which said sampling device receives at least some of said portions of said second signal; and a storage device, adapted to receive said values generated by said sampling device and to impose a delay on said values from at least one of said first and second signal.

14. A system as claimed in claim 13, wherein:

said storage device time correlates said values generated from said first signal with said values generated from said second signal.

15. A system as claimed in claim 13, wherein:

said delay corresponds to a distance between interrogation points of said respective first and second detectors.

16. A system as claimed as claim 13, wherein:

said sampling device receives a number of said portions totaling substantially all of said signals, and generates said values which represent said portions of substantially all of said signals.

17. A system as claimed in claim 13, wherein:

each of said signals is an analog signal representative of a light signal emitted from said event as detected by said detector.

18. A system as claimed in claim 13, further comprising:

an arithmetic device, adapted to arithmetically combine a designated value with each of said values generated from at least one of said signals.

19. A system as claimed in claim 18, wherein:

said arithmetic device includes a subtractor which is adapted to subtract said designated value from each of said values.

20. A system as claimed in claim 18, wherein:
said designated value is representative of an undesired signal detected by said detector.

21. A system as claimed in claim 18, wherein:
said designated value is representative of a characteristic of said detector.

22. A system as claimed in claim 13, further comprising:
a comparator, adapted to compare each of said values generated from said first signal with a respective one of said values generated from said second signal.

23. A method for processing at least two signals representative of an event detected by at least two detectors in a flow cytometer, the method comprising:
generating a first signal and a second signal representative of light emitted from said event in said flow cytometer detected using a first detector and a second detector, respectively;
receiving portions of said first signal and said second signal in time sequence, wherein said portions of said first signal are received at a time different from that during which at least some of said portions of said second signal are received;
generating a respective value representative of the respective magnitude of each respective portion of said first signal as said respective portion of said first signal is being received;
generating a respective value representative of the respective magnitude of each respective portion of said second signal as said respective portion of said second signal is being received;
storing said values generated from said first and second signals and imposing a delay on said values from at least one of said first and second signals.

24. A method as claimed in claim 23, further comprising the step of time correlating said values generated from said first signal with said values generated from said second signal.

25. A method as claimed in claim 23, wherein:
said delay corresponds to a distance between interrogation points of said respective first and second detectors.

26. A method as claimed in claim 23, wherein said receiving receives a number of said portions totaling substantially all of said signal.

27. A method as claimed in claim 23, wherein:
each said signal is an analog signal representative of a light signal emitted from said event as detected by one of said detectors.

28. A method as claimed in claim 23, further comprising:
arithmetically combining a designated value with each of said values.

29. A method as claimed in claim 28, wherein:
said arithmetic combining includes subtracting said designated value from each of said values.

30. A method as claimed in claim 28, wherein said designated value is representative of a undesired signal detected by said detector.

31. A method as claimed in claim 23, further comprising:
comparing each of said values generated from said first signal with a respective one of said values generated from said second signal.

* * * * *

(12) EX PARTE REEXAMINATION CERTIFICATE (6195th)
United States Patent
Yount et al.

(10) Number: US 6,809,804 C1
(45) Certificate Issued: Apr. 15, 2008

(54) SYSTEM AND METHOD FOR PROVIDING IMPROVED EVENT READING AND DATA PROCESSING CAPABILITIES IN A FLOW CYTOMETER

(75) Inventors: Dwayne Yount, Campbell, CA (US); Scott Brown, Santa Cruz, CA (US); Sreedhar Payavala, San Jose, CA (US); Willem Stokdijk, Livermore, CA (US); Perry Hopkins, Fremont, CA (US); Steven Helms, Scottsdale, AZ (US)

(73) Assignee: Becton Dickinson and Company, Franklin Lakes, NJ (US)

Reexamination Request:
No. 90/008,579, Apr. 9, 2007

Reexamination Certificate for:
Patent No.: 6,809,804
Issued: Oct. 26, 2004
Appl. No.: 09/853,043
Filed: May 11, 2001

Related U.S. Application Data
(60) Provisional application No. 60/203,515, filed on May 11, 2000, provisional application No. 60/203,590, filed on May 11, 2000, provisional application No. 60/203,585, filed on May 11, 2000, and provisional application No. 60/203,577, filed on May 11, 2000.

(51) Int. Cl.
*G01N 15/14* (2006.01)
*G01N 15/10* (2006.01)
*G06K 9/62* (2006.01)

(52) U.S. Cl. .................. 356/73; 250/214 DC; 250/574
(58) Field of Classification Search ...................... None
See application file for complete search history.

(56) References Cited

U.S. PATENT DOCUMENTS
5,150,313 A  9/1992  van den Engh et al.

OTHER PUBLICATIONS

Shapiro, Howard et al., "A Flow Cytomoeter Designed for Flouorescence Calibration," Cytometry, vol. 33: 280–287 (1998).

Zilmer, Nick et al., "Flow Cytometric Analysis Using Digital Signal Processing," Cytometry, vol. 20: 102–117 (1995).

*Primary Examiner*—Ovidio Escalante

(57) ABSTRACT

A system and method for use with a flow cytometer to improve event reading and data processing capabilities of the flow cytometer, while also providing efficient system configuration assessment capabilities. The system and method enables the flow cytometer to capture and sample an entire waveform representative of an event being read, and provides improved processing and analysis of the sampled data in a real time or near real-time basis. The system and method further enable the flow cytometer to assess its configuration and provide assessment results to an operator in an efficient and effective manner.

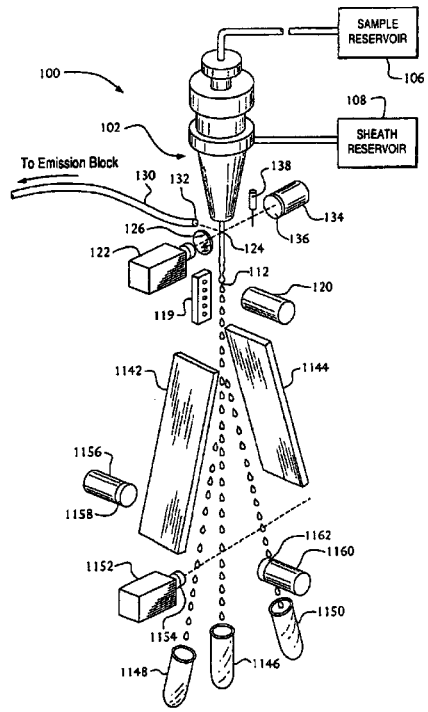

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 13–31 is confirmed.

Claims 1–12 are cancelled.

\* \* \* \* \*